(12) United States Patent
Longshaw et al.

(10) Patent No.: US 9,624,196 B2
(45) Date of Patent: Apr. 18, 2017

(54) INHIBITOR OF P38 MAP KINASE

(71) Applicants: RESPIVERT LTD, High Wycombe (GB); TOPIVERT PHARMA LTD., London (GB)

(72) Inventors: Alistair Ian Longshaw, Nottingham (GB); Euan Alexander Fraser Fordyce, Nottingham (GB); Stuart Thomas Onions, Nottingham (GB); John King-Underwood, Pendock (GB); Jennifer Venable, Solana Beach, CA (US)

(73) Assignees: RESPIVERT LTD., High Wycombe (GB); TOPIVERT PHARMA LTD., London (GB)

( * ) Notice: Subject to any disclaimer, the term of this patent is extended or adjusted under 35 U.S.C. 154(b) by 0 days.

(21) Appl. No.: 15/253,141

(22) Filed: Aug. 31, 2016

(65) Prior Publication Data

US 2016/0368896 A1  Dec. 22, 2016

Related U.S. Application Data

(63) Continuation of application No. 14/622,368, filed on Feb. 13, 2015, now Pat. No. 9,447,076.

(60) Provisional application No. 61/940,282, filed on Feb. 14, 2014, provisional application No. 61/941,064, filed on Feb. 18, 2014.

(51) Int. Cl.
  *C07D 401/12* (2006.01)
(52) U.S. Cl.
  CPC .................. *C07D 401/12* (2013.01)
(58) Field of Classification Search
  CPC .................................... C07D 401/12
  See application file for complete search history.

(56) References Cited

U.S. PATENT DOCUMENTS

| | | |
|---|---|---|
| 6,319,921 B1 | 11/2001 | Cirillo et al. |
| 6,492,393 B1 | 12/2002 | Breitfelder et al. |
| 6,492,529 B1 | 12/2002 | Kapadia et al. |
| 6,525,046 B1 | 2/2003 | Cirillo et al. |
| 6,852,717 B2 | 2/2005 | Cirillo et al. |
| 6,894,173 B2 | 5/2005 | Zhang et al. |
| 6,916,814 B2 | 7/2005 | Moss et al. |
| 7,241,758 B2 | 7/2007 | Sun et al. |
| 7,329,670 B1 | 2/2008 | Dumas et al. |
| 7,678,811 B2 | 3/2010 | Dumas et al. |
| 7,838,524 B2 | 11/2010 | Lee et al. |
| 7,838,541 B2 | 11/2010 | Dumas et al. |
| 7,928,227 B2 | 4/2011 | Boyer et al. |
| 8,071,616 B2 | 12/2011 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,455,471 B2 | 6/2013 | Wisdom et al. |
| 8,618,140 B2 | 12/2013 | Ito et al. |
| 8,642,773 B2 | 2/2014 | Ito et al. |
| 8,927,563 B2 | 1/2015 | Fyfe et al. |
| 8,933,228 B2 | 1/2015 | Murray et al. |
| 8,975,285 B2 | 3/2015 | Ito et al. |
| 9,024,041 B2 | 5/2015 | King-Underwood et al. |
| 9,108,950 B2 | 8/2015 | Ito et al. |
| 9,249,125 B2 | 2/2016 | Duffy et al. |
| 9,260,410 B2 | 2/2016 | King-Underwood et al. |
| 2004/0152725 A1 | 8/2004 | Moss et al. |
| 2008/0227828 A1 | 9/2008 | Dumas et al. |
| 2008/0300281 A1 | 12/2008 | Dumas et al. |
| 2009/0131437 A1 | 5/2009 | Furet et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0102607 A1 | 4/2013 | Cass et al. |

(Continued)

FOREIGN PATENT DOCUMENTS

| | | |
|---|---|---|
| EP | 2324825 A1 | 5/2011 |
| WO | WO 99/32110 A1 | 7/1999 |

(Continued)

OTHER PUBLICATIONS

CAS Registry No. 1379397-83-7, Jun. 18, 2012; American Chemical Society.

(Continued)

*Primary Examiner* — Brian McDowell
(74) *Attorney, Agent, or Firm* — Knobbe, Martens Olson & Bear, LLP

(57) ABSTRACT

A compound of formula (XV):

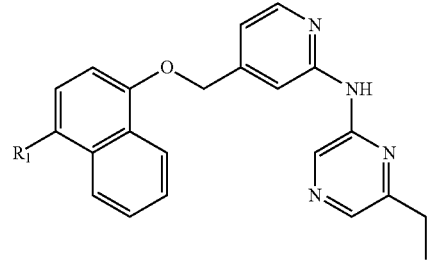

wherein $R_1$ represents an amino group, a protected amino group or nitro group; or a salt thereof. The compound is a p38 MAP kinase inhibitor. The compound and its pharmaceutically acceptable salts can be used for treatment of conditions, such as inflammatory diseases.

5 Claims, 11 Drawing Sheets

(56) References Cited

U.S. PATENT DOCUMENTS

| | | |
|---|---|---|
| 2013/0123260 A1 | 5/2013 | Charron et al. |
| 2014/0057915 A1 | 2/2014 | Cariou et al. |
| 2014/0114061 A1 | 4/2014 | Kugimoto et al. |
| 2014/0114064 A1 | 4/2014 | Ito et al. |
| 2014/0249169 A1 | 9/2014 | Ito et al. |
| 2014/0296208 A1 | 10/2014 | Baker et al. |
| 2015/0166483 A1 | 6/2015 | Fyfe |
| 2015/0210722 A1 | 7/2015 | Fyfe et al. |
| 2015/0218137 A1 | 8/2015 | Cariou et al. |
| 2015/0225373 A1 | 8/2015 | Fyfe et al. |
| 2015/0225427 A1 | 8/2015 | Fyfe et al. |
| 2015/0252024 A1 | 9/2015 | Ito et al. |
| 2015/0329523 A1 | 11/2015 | Frickel et al. |
| 2016/0009695 A1 | 1/2016 | Ito et al. |
| 2016/0016934 A1 | 1/2016 | Fyfe |
| 2016/0039797 A1 | 2/2016 | Fyfe |
| 2016/0096805 A1 | 4/2016 | Fyfe |
| 2016/0102059 A1 | 4/2016 | Baker et al. |

FOREIGN PATENT DOCUMENTS

| | | |
|---|---|---|
| WO | WO 99/32455 A1 | 7/1999 |
| WO | WO 00/43384 A1 | 7/2000 |
| WO | WO 01/04115 A1 | 1/2001 |
| WO | WO 01/36403 A1 | 5/2001 |
| WO | WO 01/64642 A1 | 9/2001 |
| WO | WO 02/092576 A1 | 11/2002 |
| WO | WO 03/005999 A1 | 1/2003 |
| WO | WO 03/068228 A1 | 8/2003 |
| WO | WO 03/068229 A1 | 8/2003 |
| WO | WO 03/072569 A1 | 9/2003 |
| WO | WO 2004/002481 A1 | 1/2004 |
| WO | WO 2004/007472 A1 | 1/2004 |
| WO | WO 2004/078746 A1 | 9/2004 |
| WO | WO 2005/110994 A1 | 11/2005 |
| WO | WO 2006/072589 A1 | 7/2006 |
| WO | WO 2007/002635 A1 | 1/2007 |
| WO | WO 2008/067027 A1 | 6/2008 |
| WO | WO 2009/117080 A1 | 9/2009 |
| WO | WO 2010/038085 A1 | 4/2010 |
| WO | WO 2010/038086 A1 | 4/2010 |
| WO | WO 2010/067130 A1 | 6/2010 |
| WO | WO 2010/067131 A1 | 6/2010 |
| WO | WO 2010/112936 A1 | 10/2010 |
| WO | WO 2011/070368 A1 | 6/2011 |
| WO | WO 2011/070369 A1 | 6/2011 |
| WO | WO 2011/121366 A1 | 10/2011 |
| WO | WO 2011/124923 A1 | 10/2011 |
| WO | WO 2011/124930 A1 | 10/2011 |
| WO | WO 2011/158039 A1 | 12/2011 |
| WO | WO 2011/158042 A1 | 12/2011 |
| WO | WO 2011/158044 A1 | 12/2011 |
| WO | WO 2013/050756 A1 | 4/2013 |
| WO | WO 2013/050757 A1 | 4/2013 |
| WO | WO 2014/027209 A1 | 2/2014 |
| WO | WO 2014/033446 A1 | 3/2014 |
| WO | WO 2014/033447 A1 | 3/2014 |
| WO | WO 2014/033448 A1 | 3/2014 |
| WO | WO 2014/033449 A1 | 3/2014 |
| WO | WO 2014/076484 A1 | 5/2014 |
| WO | WO 2014/140582 A1 | 9/2014 |
| WO | WO 2014/162121 A1 | 10/2014 |
| WO | WO 2014/162122 A1 | 10/2014 |
| WO | WO 2014/162126 A1 | 10/2014 |
| WO | WO 2015/092423 A1 | 6/2015 |
| WO | WO 2015/121444 A1 | 8/2015 |
| WO | WO 2015/121660 A1 | 8/2015 |
| WO | WO 2016/051186 A1 | 4/2016 |

OTHER PUBLICATIONS

CAS Registry No. 1379401-24-7, Jun. 18, 2012; American Chemical Society.
CAS Registry No. 1379457-84-7, Jun. 18, 2012; American Chemical Society.
CAS Registry No. 1379462-36-8, Jun. 18, 2012; American Chemical Society.
CAS Registry No. 1379462-42-6, Jun. 18, 2012; American Chemical Society.
CAS Registry No. 1384595-05-4, Jul. 27, 2012; American Chemical Society.
CAS Registry No. 1384608-34-7, Jul. 27, 2012; American Chemical Society.
CAS Registry No. 1384610-90-5, Jul. 27, 2012; American Chemical Society.
CAS Registry No. 1384611-77-1, Jul. 27, 2012; American Chemical Society.
Onions, S et al. 2016 "Discovery of narrow spectrum kinase inhibitors: New therapeutic agents for the treatment of COPD and steroid-resistant asthma," *Journal of Medicinal Chemistry* 59: 1727-1746.
To, W.S. et al. 2015 "Potent anti-inflammatory effects of the narrow spectrum kinase inhibitor RV1088 on rheumatoid arthritis synovial membrane cells" *British Journal of Pharmacology* 172: 3805-3816.

Figure 8A
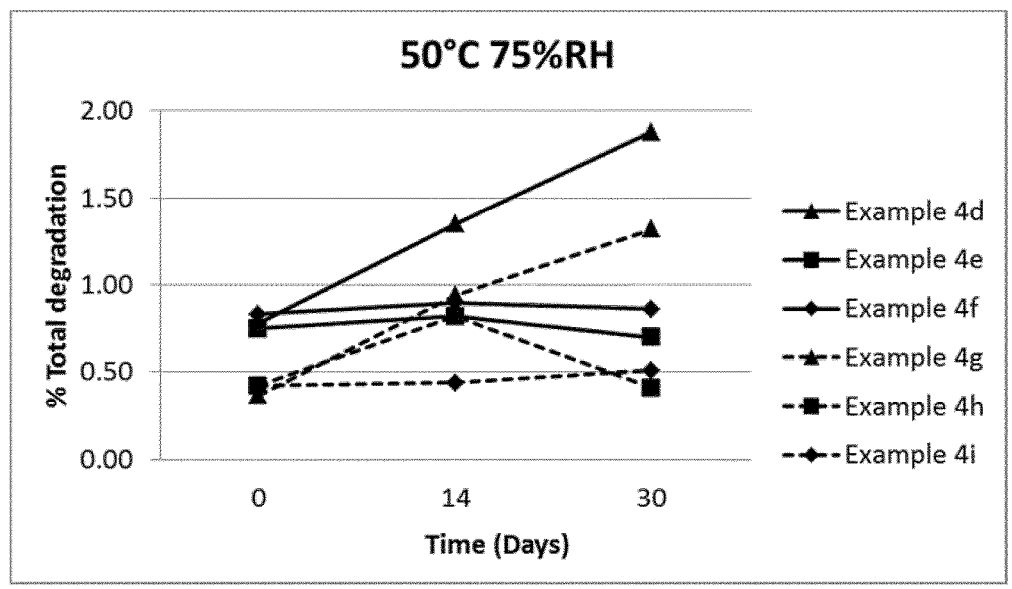
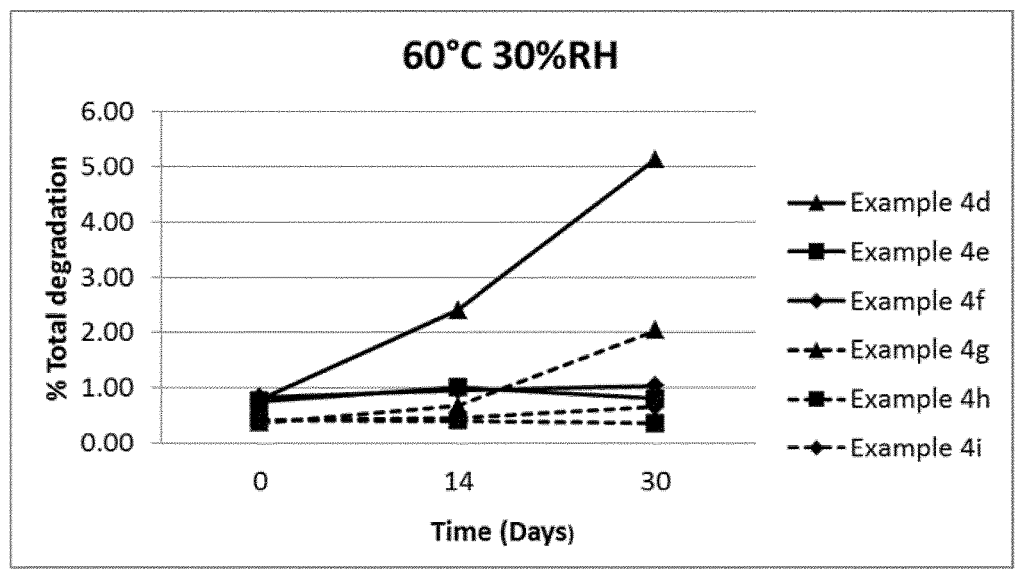
Figure 8B

Figure 8C
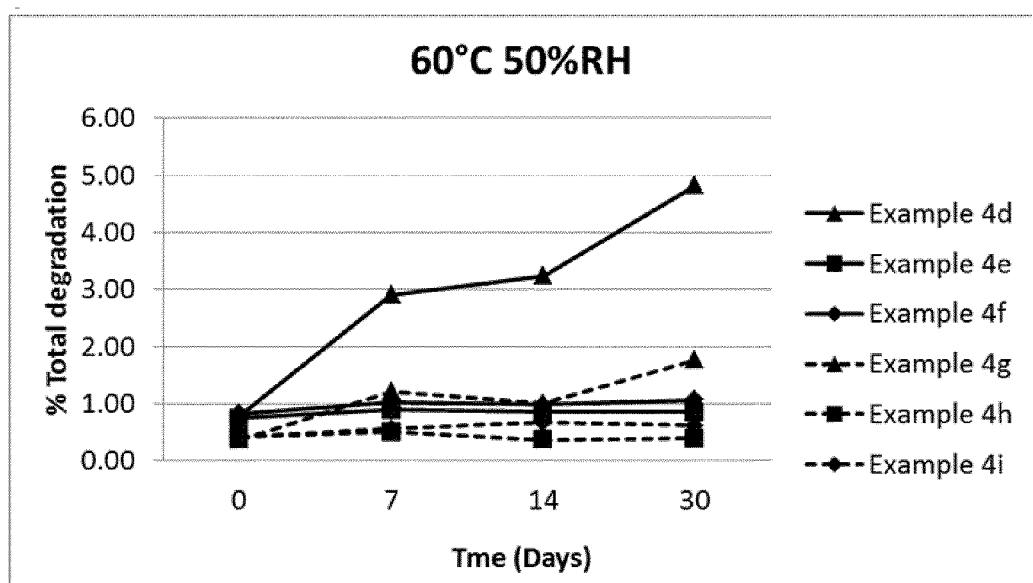
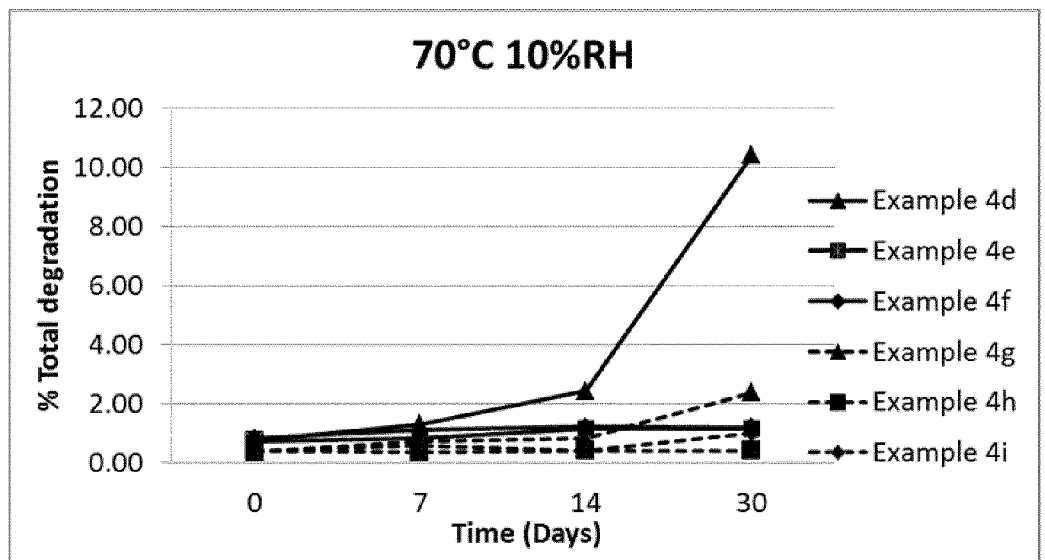
Figure 8D

Figure 8E
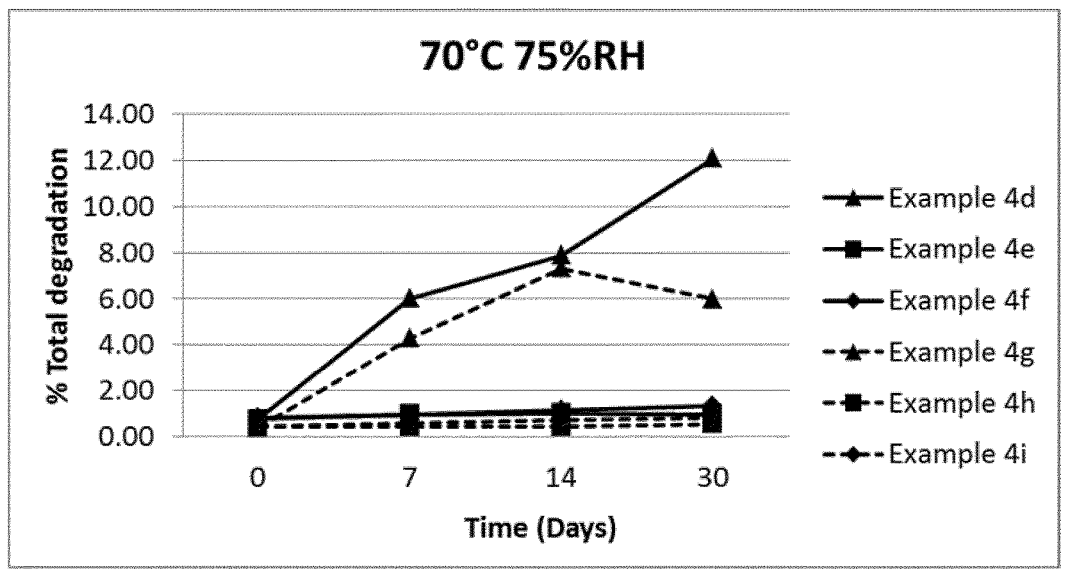
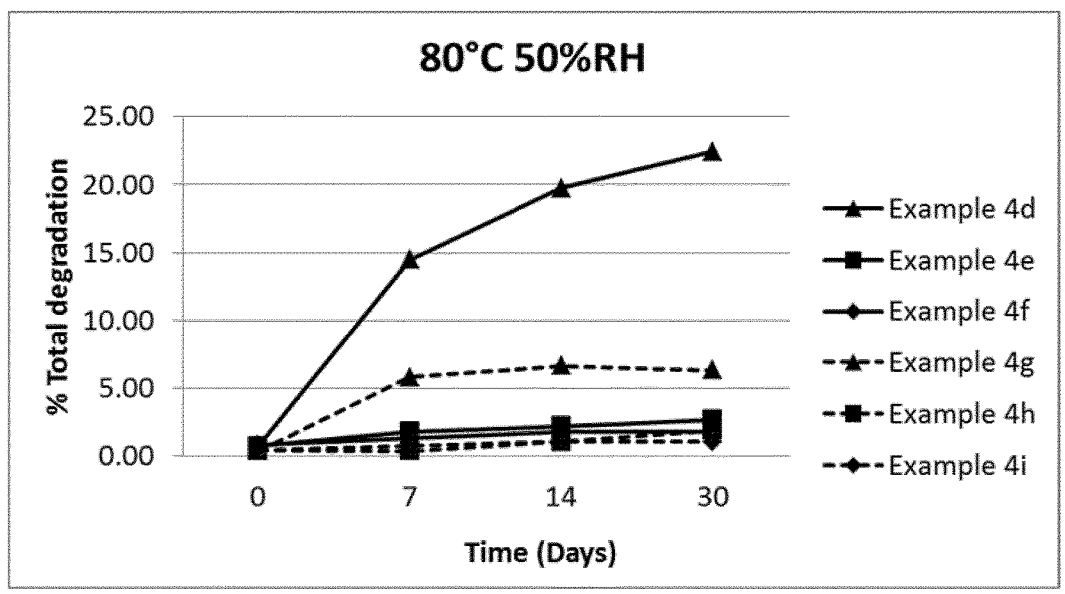
Figure 8F

INHIBITOR OF P38 MAP KINASE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The invention relates to a compound which is an inhibitor of the family of p38 mitogen-activated protein kinase enzymes (referred to herein as p38 MAP kinase inhibitors), for example the alpha and gamma kinase sub-types thereof, and the Src family of tyrosine kinases, and to its use in therapy, including in pharmaceutical combinations, especially in the treatment of inflammatory diseases, in particular inflammatory diseases of the lung, such as asthma and COPD, as well as those of the gastrointestinal tract, such as ulcerative colitis, Irritable Bowel Disease (IBD) and Crohn's disease and of the eye, such as uveitis.

BACKGROUND OF THE INVENTION

Four p38 MAPK isoforms (alpha, beta, gamma and delta respectively), have been identified each displaying different patterns of tissue expression in man. The p38 MAPK alpha and beta isoforms are found ubiquitously in the body, being present in many different cell types. The alpha isoform is well characterized in terms of its role in inflammation. Although studies using a chemical genetic approach in mice indicate that the p38 MAPK beta isoform does not play a role in inflammation (O'Keefe, S. J. et al., *J. Biol. Chem.*, 2007, 282(48), 34663-71), it may be involved in pain mechanisms through the regulation of COX2 expression (Fitzsimmons, B. L. et al., *Neuroreport*, 2010, 21(4), 313-7). These isoforms are inhibited by a number of previously described small molecular weight compounds. Early classes of inhibitors were highly toxic due to the broad tissue distribution of these isoforms which resulted in multiple off-target effects of the compounds. Furthermore, development of a substantial number of inhibitors has been discontinued due to unacceptable safety profiles in clinical studies (Pettus, L. H. and Wurz, R. P., *Curr. Top. Med. Chem.*, 2008, 8(16), 1452-67). As these adverse effects vary with chemotype, and the compounds have distinct kinase selectivity patterns, the observed toxicities may be structure-related rather than p38 mechanism-based. More recently, compounds with greater potency and specificity for p38α/β MAPK have been developed; however, levels of efficacy achieved in the treatment of chronic inflammatory diseases, including rheumatoid arthritis (SCIO-469, Genovese et al., *J. Rheumatol.*, 2011, 38, 846-54; Pamapimod, Cohen et al., *Arthritis Rheum.*, 2009, 60, 335-344; BMS-582949, Schieven et al., *Arthritis Rheum.*, 2010, 62, Suppl. 10:1513) and COPD (Losmapimod, Watz et al., *Lancet Resp. Med.*, 2014, 2, 63-72) have been disappointing. Furthermore, it is noteworthy that a p38 MAPK inhibitor was found to deliver benefit for patients with IBD after one week's treatment which was not sustained over a four week course of treatment (BIRB-796, Schreiber, S. et al., *Clin. Gastro. Hepatology*, 2006, 4, 325-334).

An important conclusion drawn from these studies is that use of a target specific kinase inhibitor may not be sufficient to achieve and sustain therapeutic benefit in complex inflammatory diseases, where dysregulation of multiple immuno-inflammatory pathways and biological adaption can by-pass blockade of a single target mechanism, resulting in the loss of response. It can be argued that for complex inflammatory disease such as COPD, rheumatoid arthritis and IBD, inhibitors that target a set of kinases that are critical for regulation of the different immuno-inflammatory mechanisms linked to pathology will have greater potential to achieve efficacy and a sustained therapeutic response.

The role of p38 MAPK-alpha in the regulation of inflammatory pathways has been investigated extensively and is well established. Less is known about the p38 MAPK gamma and delta isoforms, which, unlike the alpha and beta isozymes are expressed in specific tissues and cells. The p38 MAPK-delta isoform is expressed more highly in the pancreas, testes, lung, small intestine and the kidney. It is also abundant in macrophages and detectable in neutrophils, CD4+ T cells and in endothelial cells (Shmueli, O. et al., *Comptes Rendus Biologies*, 2003, 326(10-11), 1067-1072; Smith, S. J. *Br. J. Pharmacol.*, 2006, 149, 393-404; Hale, K. K., *J. Immunol.*, 1999, 162(7), 4246-52; Wang, X. S. et al., *J. Biol. Chem.*, 1997, 272(38), 23668-23674). Very little is known about the distribution of p38 MAPK gamma although it is expressed more highly in brain, skeletal muscle and heart, as well as in lymphocytes and macrophages (Shmueli, O. et al., *Comptes Rendus Biologies*, 2003, 326(10-11), 1067-1072; Hale, K. K., *J. Immunol.*, 1999, 162(7), 4246-52; Court, N. W. et al., *J. Mol. Cell. Cardiol.*, 2002, 34(4), 413-26; Mertens, S. et al., FEBS Lett., 1996, 383(3), 273-6). Evidence that the p38 MAPK-gamma and p38 MAPK-delta kinases are expressed in immunologically important and pro-inflammatory cell types has raised interest in their functions relative to p38 MAPK-alpha. Selective small molecule inhibitors of p38 MAPK gamma and p38 MAPK delta are not currently available to assess the roles of these kinases pharmacologically, although one previously disclosed compound, BIRB 796, is known to possess pan-isoform inhibitory activity. The inhibition of p38 MAPK gamma and delta isoforms is observed at higher concentrations of the compound than those required to inhibit p38 MAPK alpha and p38 beta (Kuma, Y., *J. Biol. Chem.*, 2005, 280, 19472-19479). In addition BIRB 796 also impaired the phosphorylation of p38 MAPKs or JNKs by the upstream kinase MKK6 or MKK4. Kuma discussed the possibility that the conformational change caused by the binding of the inhibitor to the MAPK protein may affect the structure of both its phosphorylation site and the docking site for the upstream activator, thereby impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma and in COPD (Chung, F., *Chest*, 2011, 139(6), 1470-1479). There is now an abundant literature which demonstrates that p38 MAP kinase is activated by a range of pro-inflammatory cytokines and that its activation results in the recruitment and release of additional pro-inflammatory cytokines. For instance Smith describes the inhibitory effect of p38 MAP kinase inhibitors on TNFα release from human PBMCs. However, the production of some cytokines (IL-8 and GM-CSF) by lung tissue macrophages isolated from smokers and ex-smokers was relatively insensitive to p38α/β MAPK inhibitors and Smith suggests that the abundance of p38 MAPK-delta expressed in these cells might account for the diminished effects of the compounds (Smith et al., *Br. J. Pharmacol.*, 2006, 149, 393-404). Risco et al., (*Proc. Natl. Acad. Sci.*

U.S.A., 2012, 109, 11200-11205) have used p38 MAPK-gamma and p38 MAPK-delta gene knockout mice to investigate the roles of these p38 isoforms in pathways regulating cytokine production by macrophages. These studies established that in mice both kinases are essential for innate immune inflammatory responses including proinflammatory cytokine production. More recently, Criado, G. et al., (Arthritis Rheum., 2014, 66(5), 1208-17) have demonstrated that in a mouse model of inflammatory arthritis reduced disease severity in p38γ/δ−/− mice was associated with lower cytokine production and immunological activation than in normal control mice, indicating that p38 MAPK gamma and p38 MAPK delta are crucial regulators of inflammatory joint pathology. These findings suggest that in addition to p38 MAPK alpha, p38 MAPK gamma and p38 MAPK delta are potential therapeutic targets in complex diseases that involve innate and adaptive immune responses such as COPD.

The use of inhibitors of p38 MAP kinase in the treatment of chronic obstructive pulmonary disease (COPD) has also been investigated. Small molecule inhibitors targeted to p38 MAPK α/β have proved to be effective in reducing various parameters of inflammation in cells and in tissues obtained from patients with COPD, who are generally corticosteroid insensitive, (Smith, S. J., Br. J. Pharmacol., 2006, 149, 393-404) as well as in various in vivo animal models (Underwood, D. C. et al., Am. J. Physiol., 2000, 279, L895-902; Nath, P. et al., Eur. J. PharmacoL, 2006, 544, 160-167). Irusen and colleagues have also suggested the possible involvement of p38 MAPK α/β with corticosteroid insensitivity via the reduction of binding affinity of the glucocorticoid receptor (GR) in nuclei (Irusen, E. et al., J. Allergy Clin. Immunol., 2002, 109, 649-657). Clinical experience with a range of p38 MAP kinase inhibitors, including AMG548, BIRB 796, VX702, SCIO469 and SCIO323 has been described (Lee, M. R. and Dominguez, C., Current Med. Chem., 2005, 12, 2979-2994).

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. A recent publication of Mercado (Mercado, N., et al., Mol. Pharmacol., 2011, 80(6), 1128-1135) demonstrates that silencing p38 MAPK-γ has the potential to restore sensitivity to corticosteroids. P38 MAPK alpha (Mercado, N. et al., PLoS ONE, 2012, 7(7), e41582, 1-9) and JNK (Papi et al., J. Allergy Clin. Immunol., 2013, 132, 1075-1085) have also been reported to have roles in regulating corticosteroid insensitivity and Armstrong et al. (JPET, 2011, 338, 732-740) have shown that the mixed p38 isoform inhibitor BIRB-796 and the corticosteroid dexamethasone have synergistic anti-inflammatory effects on COPD alveolar macrophages. Consequently there may be a benefit for patients in the use of a less p38 alpha-specific MAP kinase inhibitor for the treatment of COPD and severe asthma.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist.

Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

Epidemiological investigations have revealed a strong association between viral infections of the upper respiratory tract and a substantial percentage of the exacerbations suffered by patients already diagnosed with chronic respiratory diseases. Some of the most compelling data in this regard derives from longitudinal studies of children suffering from asthma (Papadopoulos, N. G. et al., Paediatr. Respir. Rev., 2004, 5(3), 255-260). A variety of additional studies support the conclusion that a viral infection can precipitate exacerbations and increase disease severity. For example, experimental clinical infections with rhinovirus have been reported to cause bronchial hyper-responsiveness to histamine in asthmatics that is unresponsive to treatment with corticosteroids (Grunberg, K., et al., Am. J. Respir. Crit. Care Med., 2001, 164(10), 1816-1822). Further evidence derives from the association observed between disease exacerbations in patients with cystic fibrosis and HRV infections (Wat, D. et al., J. Cyst. Fibros., 2008, 7, 320-328). Also consistent with this body of data is the finding that respiratory viral infections, including rhinovirus, represent an independent risk factor that correlates negatively with the 12 month survival rate in paediatric, lung transplant recipients (Liu, M. et al., Transpl. Infect. Dis., 2009, 11(4), 304-312).

TLR3 is an endosomal pathogen pattern recognition receptor that senses viral dsRNA that is produced during viral infection. In human bronchial epithelial cells (BEAS2B) the TLR3 pathway is activated in response to rhinovirus infection (RV1B and RV39) (Wang et al., J. Immunol., 2009, 183, 6989-6997). Inhaled dsRNA and rhinovirus infection evoke neutrophilic exacerbation in allergic mice with established experimental asthma (Mahmutovic-Persson et al., Allergy, 2014, 69(3), 348-358). In an allergic asthma model, rhinovirus-infected TLR3 knockout mice demonstrated reduced infiltration of neutrophils and macrophages into the lungs and significantly lower airways inflammation when compared with TLR3 positive controls (Wang, Q. et al., PLoS Pathog., 7(5), el 002070). Taken together these observations suggest that activation of the TLR3-pathway is likely to play an important role in the development of airways inflammation and exacerbations of respiratory disease in response to rhinovirus-mediated respiratory tract infections In human rhinovirus infected cells the activation of TLR3 has been shown to involve the receptor-recruitment and activation of c-Src kinase which mediates multiple downstream cellular effects. A small number of studies have appeared that link the activation of cellular Src (Src1 or p60-Src) or Src family kinases to specific responses following infection with viruses. These include a report that adenovirus elicits a P13 kinase mediated activation of Akt through a c-Src dependent mechanism. Syk kinase activity is reported to be controlled by c-Src as an upstream kinase in HRV infection (Lau et al., J. Immunol., 2008, 180, 870-880). It has also been suggested that Rhinovirus-39 induced IL-8 production in epithelial cells depends upon Src kinase activation (Bentley, J. K. et al., J. Virol., 2007, 81, 1186-1194). Finally, it has been proposed that activation of Src kinase is involved in the induction of mucin production by rhinovirus-14 in epithelial cells and sub-mucosal glands (Inoue, D. et al., *Respir. Physiol. Neurobiol.*, 2006, 154(3), 484-499).

It has been disclosed previously that compounds that inhibit p59-HCK are effective against influenza virus replication (Charron, C. E. et al., WO 2011/070369). Certain p38 MAPK inhibitors have also been described as inhibitors of the replication of respiratory syncitial virus (Cass, L. et al., WO 2011/158039).

For the reasons summarised above, compounds designed to treat chronic respiratory diseases that combine inhibition of c-Src and p59-HCK kinases with the inhibition of p38 MAPKs, are expected to be particularly efficacious.

In addition to playing key roles in cell signalling events which control the activity of pro-inflammatory pathways, kinase enzymes are now also recognised to regulate the activity of a range of cellular functions. Among those which have been discussed recently are the maintenance of DNA integrity (Shilo, Y. *Nat. Rev. Cancer*, 2003, 3, 155-168) and co-ordination of the complex processes of cell division. An illustration of recent findings is a publication describing the impact of a set of inhibitors acting upon the so-called "Olaharsky kinases" on the frequency of micronucleus formation in vitro (Olaharsky, A. J. et al., *PLoS Comput. Biol.*, 2009, 5(7), e1000446). Micronucleus formation is implicated in, or associated with, disruption of mitotic processes and is therefore an undesirable manifestation of potential toxicity. Inhibition of glycogen synthase kinase 3α (GSK3a) was found to be a particularly significant factor that increases the likelihood of a kinase inhibitor promoting micronucleus formation. Recently, inhibition of the kinase GSK3β with RNAi was also reported to promote micronucleus formation (Tighe, A. et al., *BMC Cell Biology*, 2007, 8:34).

It may be possible to attenuate the adverse effects arising from drug interactions with Olaharsky kinases, such as GSK3α, by optimisation of the dose and/or by changing the route of administration. However, it would be more advantageous to identify therapeutically useful molecules that demonstrate low or undetectable activity against these off-target enzymes and consequently elicit little or no disruption of mitotic processes, as measured in mitosis assays.

It is evident from consideration of the literature cited hereinabove that there remains a need to identify and develop new p38 MAP kinase inhibitors that have improved therapeutic potential over currently available treatments. Desirable compounds are those that exhibit a superior therapeutic index by exerting, at the least, an equally efficacious effect as previous agents but, in one or more respects, are less toxic at the relevant therapeutic dose. An objective of the present invention therefore, is to provide such a novel compound that inhibits the enzyme activity of p38 MAP kinase, for example with certain sub-type specificities (particularly alpha and gamma), as well as inhibiting the enzyme activity of tyrosine kinases within the Src family (such as p59-HCK and particularly c-Src) thereby possessing good anti-inflammatory properties, and suitable for use in therapy. The compound of the invention exhibits weak or no inhibitory activity of Olaharsky kinases, such as GSK3a and exhibits weak or no inhibitory activity of SYK kinase which contributes to its expected favourable safety profile.

SUMMARY OF THE INVENTION

According to the invention, there is provided a compound of formula (I):

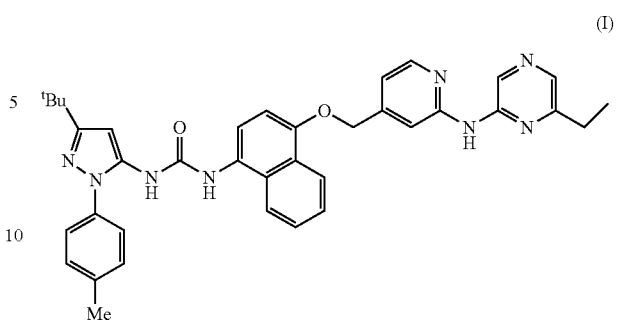

or a pharmaceutically acceptable salt thereof.

The compound of formula (I) together with its pharmaceutically acceptable salts is sometimes referred to herein as "the compound of the present invention" or similar.

BRIEF DESCRIPTION OF THE FIGURES

FIGS. 8A-8F show the results of chemical stability testing on various compositions containing the compound of the invention (in free base and maleate salt forms).

DETAILED DESCRIPTION OF CERTAIN ILLUSTRATIVE EMBODIMENTS OF THE INVENTION

Figure 1:
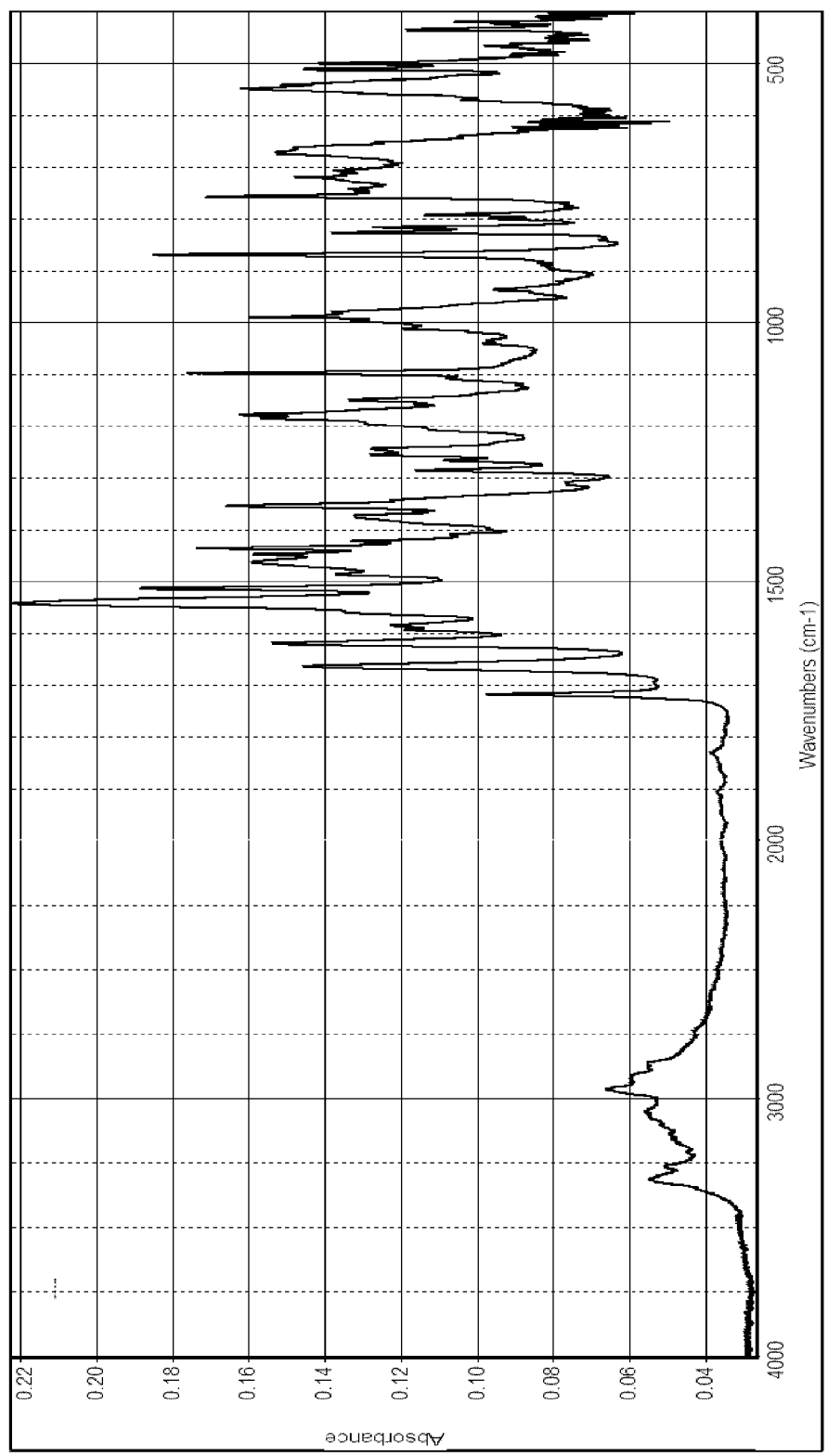
FIG. 1 shows an IR spectrum (micro ATR) of a sample of the compound of formula (I), maleate salt, Form 2

The compound of formula (I) may be prepared or employed in the form of a pharmaceutically acceptable salt, including the therapeutically active non-toxic acid addition salts that the compound of formula (I) is able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like. Preferably, the compound of formula (I) is employed in the form of its maleate salt. Conversely said salt forms can be converted by treatment with an appropriate base into the free base form.

The invention provided herein extends to all stereoisomers of the compound of formula (I). The term stereoisomers as employed herein refers to isomeric molecules that have the same molecular formula and sequence of bonded atoms (constitution), but that differ only in the three-dimensional orientations of their atoms in space.

As employed herein the definition of the compound of formula (I) is intended to include all tautomers of said compounds, and solvates of said compounds (including solvates of salts of said compounds) unless the context specifically indicates otherwise. Examples of solvates include hydrates.

The invention provided herein extends to prodrugs of the compound of formula (I), that is to say compounds which break down and/or are metabolised in vivo to provide an active compound of formula (I).

In a further aspect of the invention there is provided one or more metabolites of the compound of formula (I), in particular a metabolite that retains one or more of the therapeutic activities of the compound of formula (I). A metabolite, as employed herein, is a compound that is produced in vivo from the metabolism of the compound of formula (I), such as, without limitation, oxidative metabolites and/or metabolites generated, for example, from O-dealkylation.

The compound disclosed includes a compound where the atom specified is a naturally occurring or non-naturally occurring isotope. In one embodiment the isotope is a stable isotope. Thus the disclosed compound includes, for example deuterium containing compounds and the like.

The disclosure also extends to all polymorphic forms of the compounds herein defined.

A first process for preparing a compound of formula (I) or a protected derivative thereof comprises reacting a compound of formula (II)

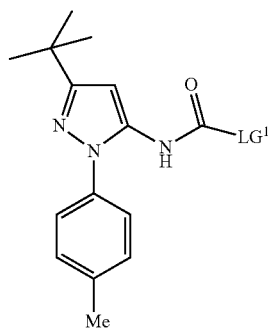

(II)

or a protected derivative thereof
wherein LG¹ represents a leaving group;
with a compound of formula (III)

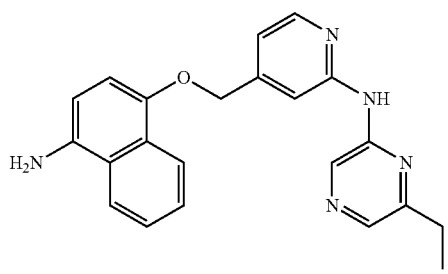

(III)

or a protected derivative thereof;

and optionally deprotecting the product to yield a compound of formula (I).

In compounds of formula (II), examples of leaving groups LG include halo (especially CI, Br) and aryloxy-, especially phenoxy-.

Suitable protecting groups and means for their removal are described infra.

Suitable conditions for the reaction of compounds of formula (II) and (III) include treating a mixture of (II) and (III) in a suitable solvent such as THF, DCM or isopropyl acetate with triethylamine or Hunig's base and warming the reaction to a temperature such as 40° C.

A second process for preparing a compound of formula (I) comprises reacting a compound of formula (IV)

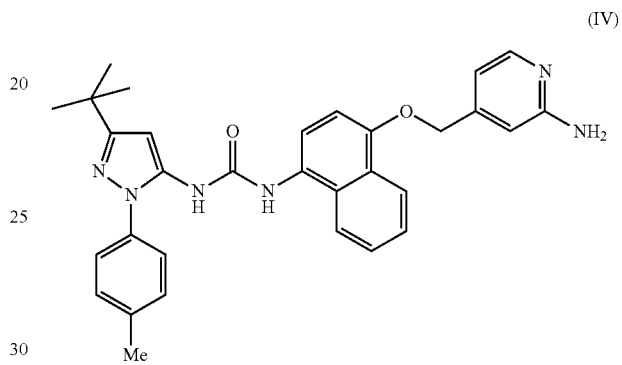

(IV)

or a protected derivative thereof,
with a compound of formula (V)

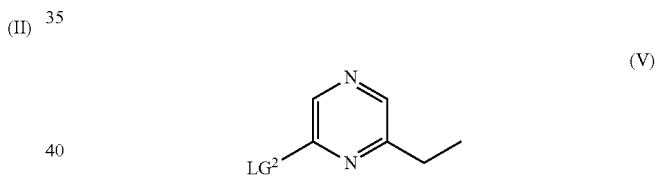

(V)

wherein LG² represents leaving group, such as halo and especially CI
or a protected derivative thereof
and optionally deprotecting the product to yield a compound of formula (I).

Suitable protecting groups and means for their removal are described infra.

Suitable conditions for the reaction of compounds of formula (IV) and (V) include those normally employed for the Buchwald reaction i.e. treatment of a solution of (IV) and (V) in a solvent such as 1,4-dioxane with a palladium source and ligand such as Pd$_2$(dba)$_3$ and BINAP and a base such as sodium tert-butoxide or cesium carbonate at elevated temperature.

Alternative ligands include diphenylphosphinoferrocene and triphenylphosphine; alternative palladium sources include palladium (II) acetate and tetrakis(triphenylphosphine)palladium(0); alternative bases include lithium bis(trimethylsilyl)amide and potassium phosphate; alternative solvents include THF and toluene. For a wider range of conditions, see Surry, D. S., Buchwald, S. L. (2008), "Biaryl Phosphane Ligands in Palladium-Catalyzed Amination", Angew. Chem. Int. Ed., 47, 6338-6361, and references therein.

Compounds of formula (II) may be prepared by reaction of a compound of formula (VI)

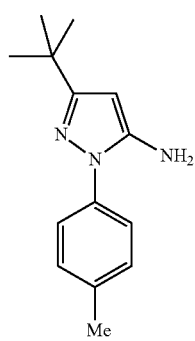
(VI)

with a compound of formula LG$^1$C(=O)LG$^3$ wherein LG$^3$ represents a leaving group such as halo and especially Cl.

Suitable conditions for the reaction of a compound of formula (VI) with a compound of formula LG$^1$C(=O)LG$^3$ where LG$^1$ is PhO and LG$^3$ is Cl comprise treatment of a mixture of a solution of compound of formula (VI) in a solvent such as isopropyl acetate and an aqueous solution of an inorganic base such as sodium carbonate with phenyl chloroformate.

Compounds of formula (VI) are known or may be prepared by methods known to persons skilled in the art.

A first process for preparing a compound of formula (III) comprises reducing a compound of formula (VII)

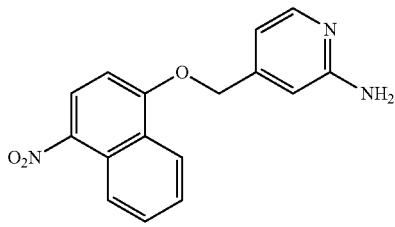
(VII)

Suitable conditions for the reduction of a compound of formula (VII) include treatment with hydrogen gas over platinum on carbon catalyst. This reaction may be carried out at elevated pressure in a solvent such as THF acidified with acetic acid. Alternatively it may be performed in a solvent such as DCM/MeOH under flow conditions using an H-cube hydrogenator.

A second process for preparing a compound of formula (III) comprises deprotecting a compound of formula (VIII)

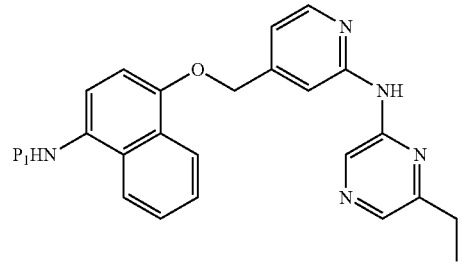
(VIII)

wherein P$_1$ represents an amine protecting group.

Suitable protecting groups and means for their removal are described infra. A most suitable protecting group is Boc which can be removed by treatment with acid such as TFA or HCl.

A first process for preparing a compound of formula (VII) comprises reacting a compound of formula (IX)

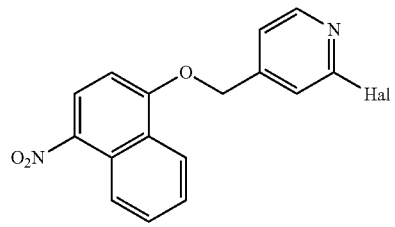
(IX)

with a compound of formula (X)

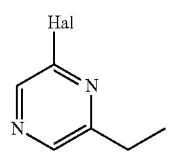
(X)

wherein Hal represents halogen, especially Cl.

Suitable conditions for the reaction of compounds of formula (IX) and (X) include those mentioned above for the reaction of compounds of formula (IV) and (V).

A second process for preparing a compound of formula (VII) comprises reacting a compound of formula (XI)

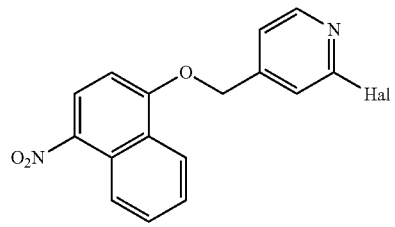
(XI)

wherein Hal represents halogen, especially Cl
with a compound of formula (XII)

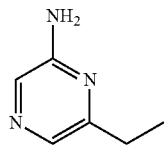
(XII)

Suitable conditions for the reaction of compounds of formula (XI) and (XII) include treatment of a solution of (XI) and (XII) in a solvent such as 1,4-dioxane with a palladium source and ligand such as $Pd_2(dba)_3$ and BINAP and a base such as sodium tert-butoxide or cesium carbonate at elevated temperature.

A first process for preparing a compound of formula (VIII) comprises reacting a compound of formula (XIII)

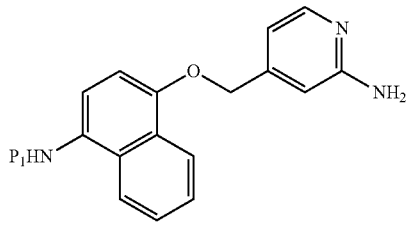
(XIII)

with a compound of formula (X)

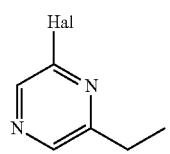
(X)

wherein Hal represents halogen, especially Cl.

Suitable conditions for the reaction of compounds of formula (XIII) and (X) are the same as those described above for the reaction of compounds of formula (IX) and (X).

A second process for preparing compounds of formula (VIII) comprises reacting a compound of formula (XIV)

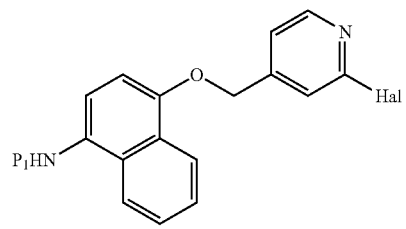
(XIV)

wherein Hal represents halogen, especially Cl
with a compound of formula (XII)

(XII)

Suitable conditions for the reaction of compounds of formula (XIV) and (XII) are the same as those described above for the reaction of compounds of formula (XI) and (XII).

Compounds of formula (IX) may be prepared as shown in the scheme below:

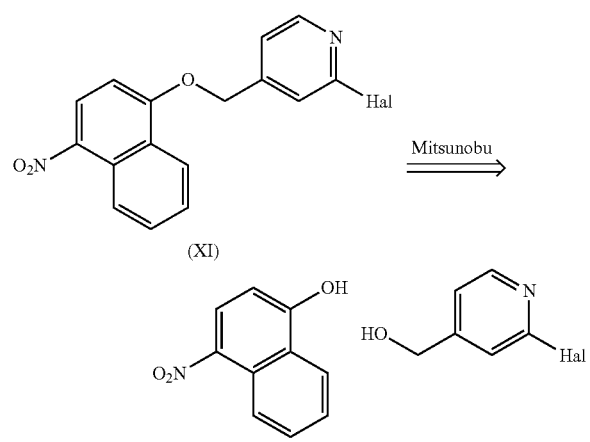

The reagents of this process are known compounds. Mitsunobu conditions include treatment of a mixture of a phenol and an alcohol with triphenylphosphine and diisopropylazodicarboxylate in a solvent such as THF. For a wider range of conditions, see Swamy, K. C.; Kumar, N. N.; Balaraman, E.; Kumar, K. V. (2009). "Mitsunobu and Related Reactions: Advances and Applications" *Chemical Reviews* 109 (6): 2551-2651, and references therein.

Compounds of formula (XI) may be prepared as shown in the scheme below:

The reagents of this process are known compounds. Mitsunobu conditions include those given above.

Compounds of formula (XIII) may be prepared as shown in the scheme below:

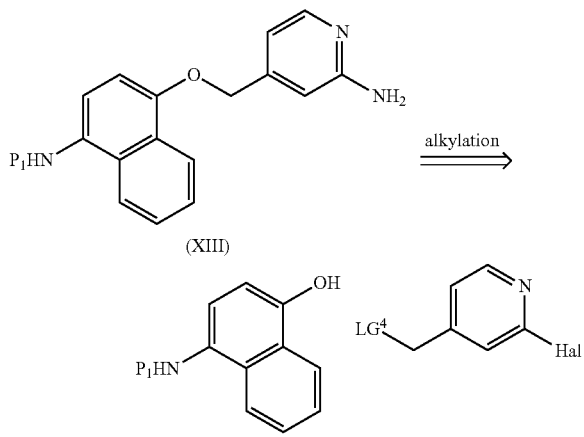

wherein LG$^4$ is a leaving group such as halo, especially Cl.

The reagents of this process are known compounds. Alkylation conditions include treatment of a mixture of a phenol and an alkyl halide with a base such as cesium or potassium carbonate in a solvent such as acetonitrile or DMF optionally at elevated temperature.

Compounds of formula (XIV) may be prepared as shown in the scheme below:

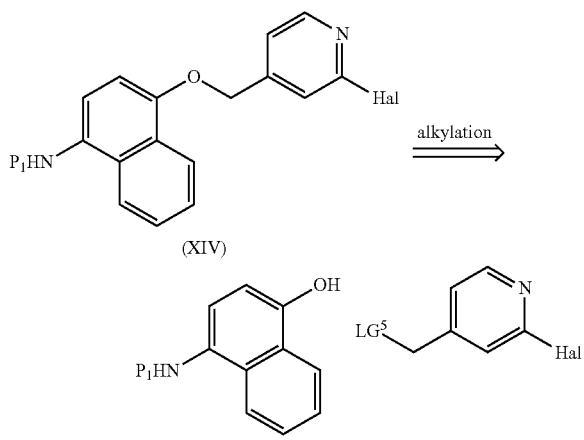

wherein LG$^5$ is a leaving group such as those mentioned above for LG$^4$.

The reagents of this process are known compounds. Alkylation conditions include those given above.

Compounds of formula (IV), (V), (VI), (X) and (XII) are either known or may be prepared by methods known to the skilled person. In respect of compound of formula (IV) see, for example, WO2010/067131, and specifically the compound structure referred to as "Intermediate A". In respect of compound of formula (VI) see, for example, WO00/043384, and specifically compound of formula LXVII.

An apparently stable crystalline unsolvated form of the free base form of the compound of the invention may be obtained by recrystallisation from solution (preferably hot, e.g. reflux temperature) in acetonitrile. In case another form is produced, this form may be obtained by slurrying in acetonitrile.

As noted above, the maleate salt is a form of the compound of the invention of particular interest. The maleate salt may be prepared by treating the free base form of the compound of the invention with maleic acid in a suitable solvent.

In a preferred process, the maleate salt is prepared by treating a solution of the compound of the invention in 2-butanone with a solution of maleic acid in 2-butanone. Crystallisation is allowed to occur, which may be assisted with seeding. The maleate salt as its Form 2 crystalline polymorph is prepared this way. The Form 2 crystalline polymorph may also be obtained by cooling a hot solution of the maleate salt of the compound of the invention in 2-butanone, e.g. from 50° C. to room temperature. Crystallisation is allowed to occur, which may be assisted with seeding.

Figure 2:
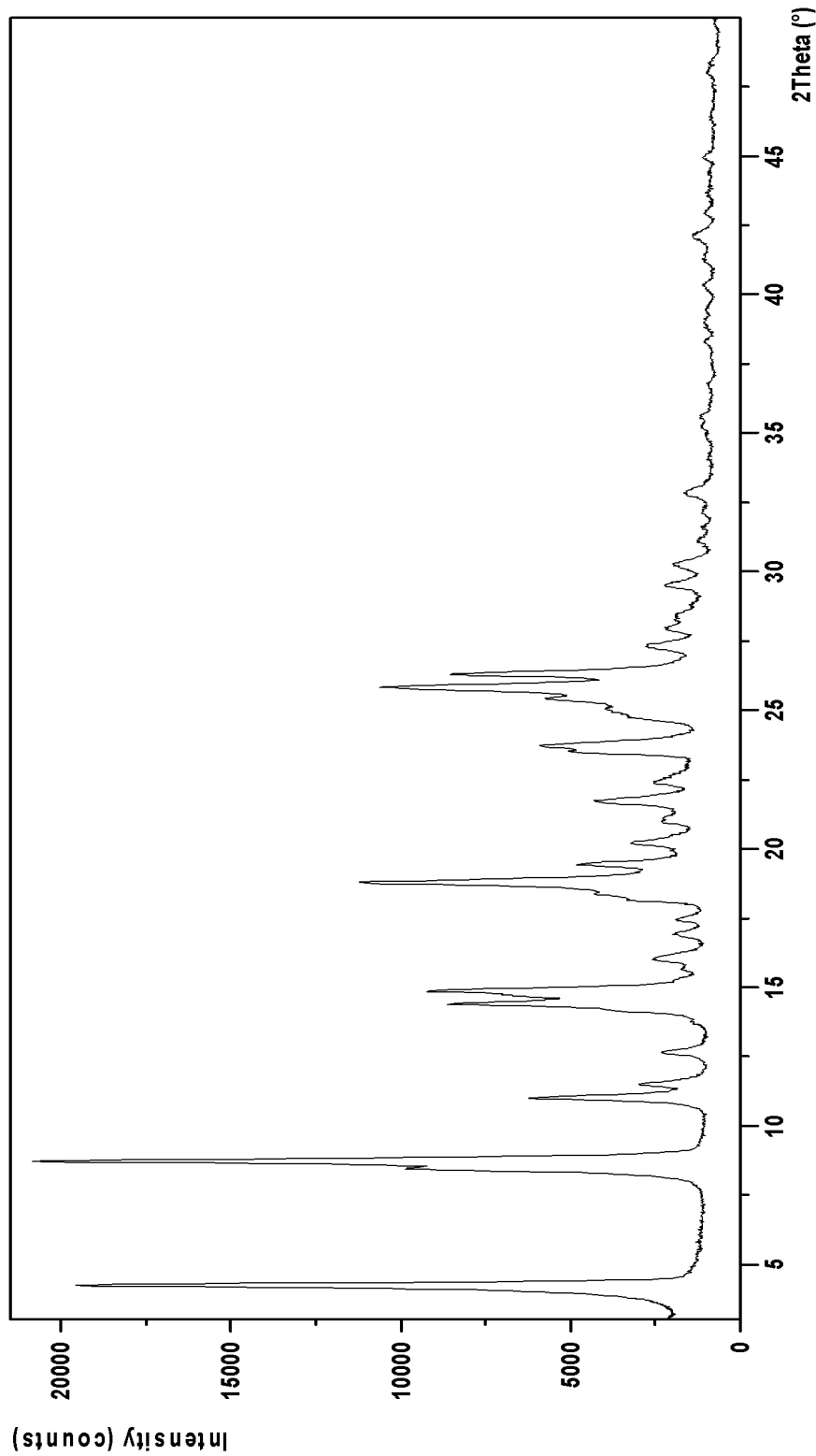
FIG. 2 shows a powder XRD pattern of a sample of the compound of formula (I), maleate salt, Form 2

The Form 2 crystalline polymorph of the maleate salt of the compound of the invention is characterised by having peak positions in a powder XRD pattern at 4.2, 8.4, 8.7, 11.0, 11.5, 12.6, 14.4, 14.9, 16.0, 17.0, 17.4, 18.8, 19.5, 20.2, 21.7, 22.4, 23.8, 25.8 and 26.3 (±0.2) degrees 2-theta (see FIG. 2). The peaks (the doublet) at 8.4 and 8.7 (±0.2) degrees 2-theta are especially characteristic for the Form 2 crystalline polymorph since peaks in these positions are absent in the XRD pattern of the Form 1 crystalline polymorph.

The Form 2 crystalline polymorph has a high melting point (approx 199° C.) with a plate like morphology.

Another crystalline form of the maleate salt of the compound of the invention was identified following recrystallisation from THF which has less favourable properties than those of Form 2. It has needle like morphology and a lower melting point, approx 148° C. This crystalline form is referred to as Form 1.

Figure 3:
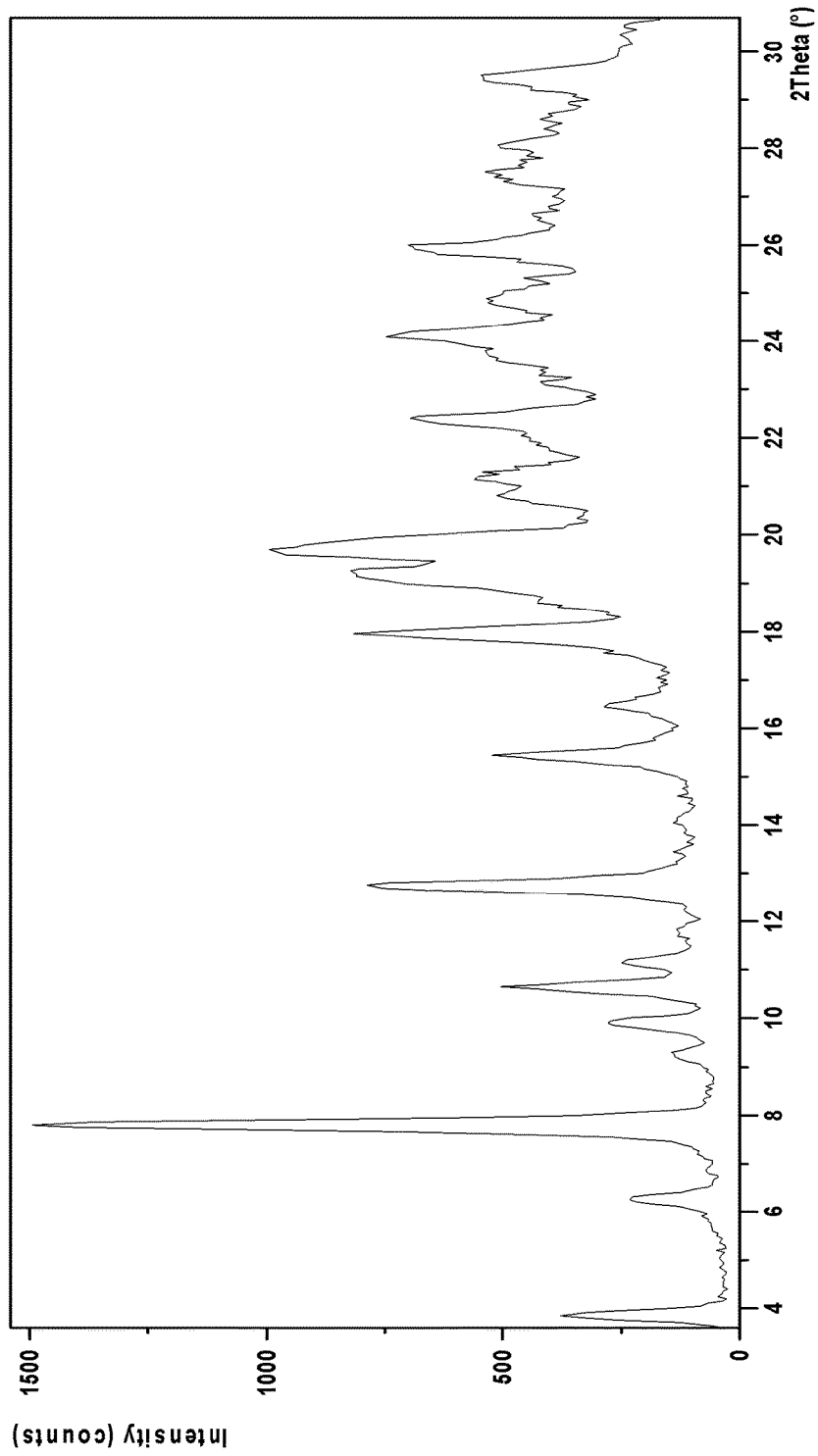
FIG. 3 shows a powder XRD pattern of a sample of the compound of formula (I), maleate salt, Form 1

The Form 1 crystalline polymorph of the maleate salt of the compound of the invention is characterised by having peak positions in a powder XRD pattern at 3.8, 6.3, 7.8, 9.3, 9.9, 10.7, 11.2, 12.7, 15.4, 16.5, 17.9, 19.2 and 19.6 (±0.2) degrees (see FIG. 3). The peaks at 6.3, 7.8 and 9.9 (±0.2) degrees 2-theta are especially characteristic for the Form 1 crystalline polymorph since peaks in these positions are absent in the XRD pattern of the Form 2 crystalline polymorph.

Thus the Form 2 polymorph is characterised by having an XRD diffraction pattern containing 10, 11, 12, 13, 14, 15, 16, 17, 18 or more preferably 19 peak positions selected from 4.2, 8.4, 8.7, 11.0, 11.5, 12.6, 14.4, 14.9, 16.0, 17.0, 17.4, 18.8, 19.5, 20.2, 21.7, 22.4, 23.8, 25.8 and 26.3 (±0.2) degrees 2-theta preferably including peaks at 8.4 and 8.7 (±0.2) degrees 2-theta and not containing peaks at 6.3, 7.8 and 9.9 (±0.2) degrees 2-theta.

In relation to FIGS. 2 and 3, it will be understood that intensity variations in XRD patterns can occur due to processes which influence intensities, such as the processing history of the sample.

Salts of the compound of the invention which are crystalline but of lesser interest than the maleate salt include hydrobromide, phosphate, tartrate, fumarate and mesylate salts.

Protecting groups may be required to protect chemically sensitive groups during one or more of the reactions described above, to ensure that the process is efficient. Thus if desired or necessary, intermediate compounds (including compounds of formula (II) to (V) as highlighted above as well as compounds of formula (VI) to (XIV)) may be protected by the use of conventional protecting groups. Protecting groups and means for their removal are described in "Protective Groups in Organic Synthesis", by Theodora W. Greene and Peter G. M. Wuts, published by John Wiley & Sons Inc; 4th Rev Ed., 2006, ISBN-10: 0471697540. Thus exemplary amine protecting groups include Boc which may be removed by TFA and exemplary alcohol protecting groups are THP which may be removed by HCl.

Compounds of formula (III) (together with derivatives thereof in which the amino group is protected, such as the compound of formula (VIII)) and the compound of formula (VII) are novel. These novel compounds, together with their salts (including pharmaceutically acceptable salts) are claimed as aspects of the invention.

Hence, the invention extends to a compound of formula (III)

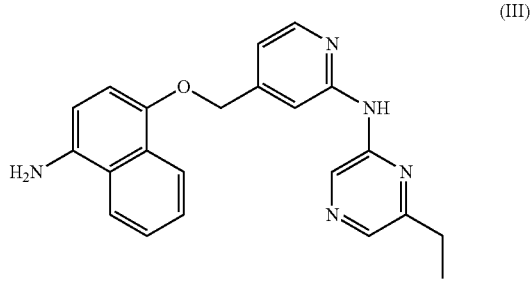 [SMILES: CCc1cncc(Nc2cc(COc3ccc(N)c4ccccc34)ccn2)n1]

(III)

or a derivative thereof in which the amino group is protected, or a salt thereof; for example a compound of formula (VIII)

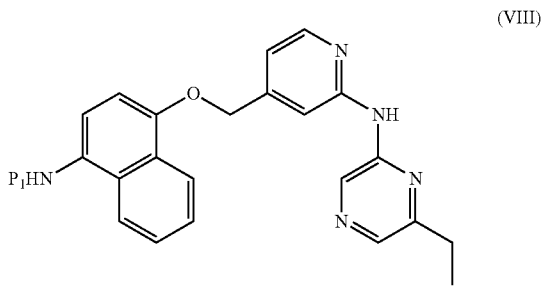

(VIII)

wherein $P_1$ represents an amine protecting group;
or a salt thereof; as well as a compound of formula (VII)

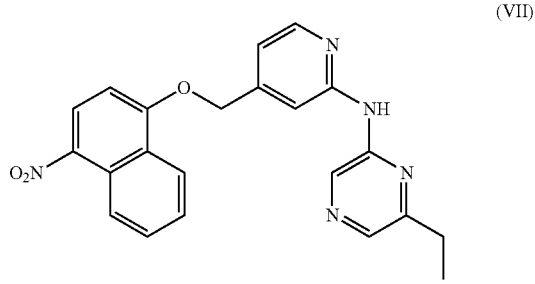 [SMILES: CCc1cncc(Nc2cc(COc3ccc([N+](=O)[O-])c4ccccc34)ccn2)n1]

(VII)

or a salt thereof.

The compound of formula (I) is a p38 MAP kinase inhibitor (especially an inhibitor of the alpha subtype) and in one aspect the compound of the present invention is provided for use as a medicament e.g. in the treatment of inflammatory diseases, for example COPD and/or asthma.

The compound of formula (I) is expected to be potent in vivo.

Typically, the prior art compounds developed to date have been intended for oral administration. This strategy involves optimizing the pharmacokinetic profile of drug substances in order to achieve an adequate duration of action. In this manner a sufficiently high drug concentration is established and maintained between doses to provide sustained clinical benefit. The inevitable consequence of this approach is that all bodily tissues, and especially the liver and the gut, are likely to be exposed to supra-therapeutically active concentrations of the drug, whether or not they are adversely affected by the disease being treated.

An alternative strategy is to design treatment paradigms in which the drug is dosed directly to the inflamed organ, that is, to exploit topical administration. Whilst this approach is not suitable for treating all chronic inflammatory diseases, it has been exploited in lung disorders, such as asthma and COPD; in skin diseases, for example against atopic dermatitis and psoriasis; for nasal conditions, typified by allergic rhinitis; and in gastrointestinal diseases, such as ulcerative colitis, IBD and Crohn's disease and inflammatory diseases of the eye, such as uveitis.

In topical therapy, one way in which efficacy can be achieved is by the use of a drug that has a sustained duration of action and is retained in the relevant organ, thereby minimizing the risk of systemic toxicity. Alternatively, in some cases, a formulation can be developed that generates a "reservoir" of the active drug which is available to sustain its desired effects. The first approach is exemplified by the anticholinergic drug tiotropium (Spiriva). This compound is administered topically to the lung as a treatment for COPD, and has an exceptionally high affinity for its target receptor resulting in a very slow off rate and consequently displays a sustained duration of action.

In one aspect of the disclosure of the compound of formula (I) it is particularly suitable for topical delivery, such as topical delivery to the lungs, in particular for the treatment of respiratory disease, for example chronic respiratory diseases such as COPD and/or asthma.

In one embodiment the compound of formula (I) is suitable for sensitizing patients to treatment with a corticosteroid who have become refractory to such treatment regimens.

The compound of formula (I) may have antiviral properties, for example the ability to prevent the infection of cells (such as respiratory epithelial cells) with a picornavirus, in particular a rhinovirus, influenza or respiratory syncytial virus.

Thus the compounds are thought to be antiviral agents, in particular suitable for the prevention, treatment or amelioration of picornavirus infections, such as rhinovirus infection, influenza or respiratory syncytial virus.

In one embodiment the compound of formula (I) is able to reduce inflammation induced by viral infection, such as rhinovirus infection and in particular viral infections that result in the release of cytokines such as IL-8, especially in vivo. This activity may, for example, be tested in vitro employing a rhinovirus induced IL-8 assay as described in the Examples herein.

In one embodiment the compound of formula (I) is able to reduce ICAM1 expression induced by rhinovirus, especially in vivo. ICAM1 is the receptor mechanism used by so-called major groove rhinovirus serotypes to infect cells. This activity may be measured, for example by a method described in the Examples herein.

It is expected that the above properties render the compound of formula (I) particularly suitable for use in the treatment (including prophylaxis) of exacerbations of inflammatory diseases, in particular viral exacerbations, or in the treatment of viral infections, in patients with one or more chronic conditions such as congestive heart failure, COPD, asthma, diabetes, cancer and/or in immunosuppressed patients, for example post-organ transplant. Such use may be in combination with anti-viral agents such as zanamivir, oseltamivir (for example oseltamivir phosphate) peramivir or laninamivir.

In general, the compound of formula (I) may be useful in the treatment of one or more conditions having an inflammatory component which, suitably, may be treated by topical or local therapy.

In particular, the compound of formula (I) may be useful in the treatment of one or more respiratory disorders including COPD (including chronic bronchitis and emphysema), asthma, paediatric asthma, cystic fibrosis, sarcoidosis, idiopathic pulmonary fibrosis, allergic rhinitis, rhinitis and sinusitis, especially asthma, or COPD (including chronic bronchitis and emphysema).

Thus the compound of formula (I) may be useful in the treatment of lung inflammation (and symptoms thereof) in subjects suffering from cystic fibrosis.

The compound of formula (I) may be useful in the treatment of eye diseases or disorders including keratoconjunctivitis sicca (dry eye), allergic conjunctivitis, conjunctivitis, diabetic retinopathy, macular oedema (including wet macular oedema and dry macular oedema), post-operative cataract inflammation or, particularly, uveitis (including posterior, anterior and pan uveitis).

The compound of formula (I) may be useful in the treatment of skin diseases or disorders including allergic dermatitis, contact dermatitis, atopic dermatitis or psoriasis.

The compound of formula (I) may be useful in the treatment of gastrointestinal diseases or disorders including ulcerative colitis, IBD or Crohn's disease.

The compound of formula (I) may be useful in the treatment of joint diseases or disorders including rheumatoid arthritis or osteoarthritis and particularly inflamed joints secondary to such conditions.

The compound of formula (I) may be useful in the treatment of cancers including cancer of the stomach and in the inhibition of the growth and metastasis of tumours including lung cancers such as non-small cell lung carcinoma, gastric carcinoma, colorectal carcinomas and malignant melanoma.

It is also expected that the compound of formula (I) may be useful in the treatment of certain other conditions including periodontitis, gingivitis and pharyngitis.

Compound of formula (I) may also re-sensitise the patient's condition to treatment with a corticosteroid, when the patient's condition has become refractory to the same.

Furthermore, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

The present invention also provides a process for preparing such a pharmaceutical composition (for example a pharmaceutical composition for parenteral, oral, topical, mucosal or rectal administration), said process comprising mixing the ingredients.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules or in the form of liquid solutions or suspensions; for topical e.g. pulmonary or intranasal administration, particularly in the form of powders, aqueous solutions or suspensions, nasal drops or aqueous or non-aqueous aerosols, and for transdermal administration e.g. patches, creams, ointments; for mucosal administration e.g. to buccal, sublingual or vaginal mucosa, and for rectal administration e.g. in the form of a suppository, cream, ointment or foam.

The compositions may conveniently be administered in unit or multi-dose dosage forms and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions or suspensions for use in the form of nasal drops or metered sprays. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably a compound of formula (I) is administered topically to the lung, eye or bowel. Hence we provide according to the invention a pharmaceutical composition comprising a compound of the present invention optionally in combination with one or more topically acceptable diluents or carriers.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC).

Suitable CFC propellants include trichloromonofluoromethane (propellant 11), dichlorotetrafluoromethane (propellant 114), and dichlorodifluoromethane (propellant 12).

Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. These may be administered by means of a nebuliser e.g. one that can be hand-held and portable or for home or hospital use (ie non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{50}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean diameter (MMAD) of 1-10 μm or a $D_{50}$ of 0.5-10 μm e.g. around 1-5 μm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. a mass mean diameter (MMAD) of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is a-lactose monohydrate.

Dry powder formulations may also contain other excipients. Thus in one embodiment a dry powder formulation according the present disclosure comprises magnesium or calcium stearate. Such formulations may have superior chemical and/or physical stability especially when such formulations also contain lactose.

A dry powder formulation is typically delivered using a dry powder inhaler (DPI) device. Example dry powder delivery systems include SPINHALER®, DISKHALER®, TURBOHALER®, DISKUS®, SKYEHALER®, ACCUHALER® and CLICKHALER®. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of the present invention is provided as a micronized dry powder formulation, for example comprising lactose of a suitable grade.

Thus, as an aspect of the invention there is provided a pharmaceutical composition comprising a compound of the invention in particulate form in combination with particulate lactose, said composition optionally comprising magnesium stearate.

In one embodiment a compound of the present invention is provided as a micronized dry powder formulation, comprising lactose of a suitable grade and magnesium stearate, filled into a device such as DISKUS. Suitably, such a device is a multidose device, for example the formulation is filled into blisters for use in a multi-unit dose device such as DISKUS.

In another embodiment a compound of the present invention is provided as a micronized dry powder formulation, for example comprising lactose of a suitable grade, filled into hard shell capsules for use in a single dose device such as AEROLISER.

In another embodiment a compound of the present invention is provided as a micronized dry powder formulation, comprising lactose of a suitable grade and magnesium stearate, filled into hard shell capsules for use in a single dose device such as AEROLISER.

In another embodiment a compound of the present invention is provided as a fine powder for use in an inhalation dosage form wherein the powder is in fine particles with a $D_{50}$ of 0.5-10 pm e.g. around 1-5 μm, that have been produced by a size reduction process other than jet mill micronisation e.g. spray drying, spray freezing, microfluidisation, high pressure homogenisation, super critical fluid crystallisation, ultrasonic crystallisation or combinations of these methods thereof, or other suitable particle formation methods known in the art that are used to produce fine particles with an aerodynamic particle size of 0.5-10 μm. The resultant particle size distribution may be measured using laser diffraction (e.g. with a Malvern Mastersizer 2000S instrument). The particles may either comprise the compound alone or in combination with suitable other excipients that may aid the processing. The resultant fine particles may form the final formulation for delivery to humans or may optionally be further formulated with other suitable excipients to facilitate delivery in an acceptable dosage form.

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of the present invention will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of the compound of the present invention. In addition, the compound of the present invention may also be introduced by means of ocular implants or inserts.

The compositions administered according to the present invention may also include various other ingredients, including, but not limited to, tonicity agents, buffers, surfactants, stabilizing polymer, preservatives, co-solvents and viscosity building agents. Suitable pharmaceutical compositions of the present invention include a compound of the invention formulated with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of the present invention. The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/ balance "HLB" in the range of 12.4 to 13.2 and are acceptable for ophthalmic use, such as TritonX114 and tyloxapol.

Additional agents that may be added to the ophthalmic compositions of compounds the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen(R), specifically Carbomer 974p (polyacrylic acid), at 0.1-0.5% w/w.

Other compounds may also be added to the ophthalmic compositions of the compound of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compound of the present invention, and hence the amount of the compound of the invention that should be included in any particular pharmaceutical formulation (whether in unit dosage form or otherwise).

A compound of formula (I) has therapeutic activity. Thus, in a further aspect, the present invention provides a compound as described herein for use in the treatment of one or more of the above mentioned conditions.

In a further aspect, the present invention provides use of a compound as described herein for the manufacture of a medicament for the treatment of one or more of the above mentioned conditions.

In a further aspect, the present invention provides a method of treatment of one or more of the above mentioned conditions which comprises administering to a subject an effective amount of a compound of the present invention or a pharmaceutical composition comprising the compound.

The word "treatment" is intended to embrace prophylaxis as well as therapeutic treatment. Treatment of conditions or disorders also embraces treatment of exacerbations thereof.

A compound of the present invention may also be administered in combination with one or more other active ingredients e.g. active ingredients suitable for treating the above mentioned conditions.

For example, possible combinations for treatment of respiratory disorders include combinations with steroids (e.g. budesonide, beclomethasone dipropionate, fluticasone propionate, mometasone furoate, fluticasone furoate, ciclesonide), beta agonists (e.g. terbutaline, salbutamol, salmeterol, formoterol, vilanterol, olodaterol, indacaterol, reproterol, fenoterol), xanthines (e.g. theophylline), anticholinergics or muscarinic antagonists (e.g. ipratropium, tiotropium, aclidinium, umeclidinium or glycopyrronium for example as the bromide salt), PI3 kinase inhibitors and anti-viral agents (e.g. zanamivir, oseltamivir, for example as the phosphate, peramivir and laninamivir).

In one embodiment there is provided a compound of the invention for use as a medicament to be administered in combination with one or more further active ingredients e.g. selected from corticosteroids, beta agonists, xanthines, muscarinic antagonists and PI3 kinase inhibitors. Suitably the beta agonist is a beta2 agonist.

In one embodiment the compound of the disclosure is administered by inhalation and a corticosteroid is administered orally or by inhalation either in combination or separately.

In one embodiment the compound of the disclosure is administered by inhalation and a beta2 agonist is administered orally or by inhalation either in combination or separately.

In one embodiment the compound of the disclosure is administered by inhalation and a muscarinic antagonist is administered orally or by inhalation either in combination or separately.

In one embodiment the compound of the disclosure is administered by inhalation either in combination or separately with one or more of a corticosteroid, a beta2 agonist and a muscarinic antagonist, all administered either orally or by inhalation.

Further, for the treatment of gastrointestinal disorders (such as Crohn's disease or ulcerative colitis), possible combinations include combinations with, for example, one or more agents selected from the list comprising:

5-aminosalicylic acid, or a prodrug thereof (such as sulfasalazine, olsalazine or bisalazide);
  corticosteroids (e.g. prednisolone, methylprednisolone, or budesonide);
  immunosuppressants (e.g. cyclosporin, tacrolimus, methotrexate, azathioprine or 6-mercaptopurine);
  anti-TNFα antibodies (e.g. infliximab, adalimumab, certolizumab pegol or golimumab);
  anti-IL12/IL23 antibodies (e.g. ustekinumab) or small molecule IL12/IL23 inhibitors (e.g., apilimod);
  Anti-α4β7 antibodies (e.g. vedolizumab);
  MAdCAM-1 blockers (e.g. PF-00547659);
  antibodies against the cell adhesion molecule a4-integrin (e.g. natalizumab);
  antibodies against the IL2 receptor a subunit (e.g. daclizumab or basiliximab);
  JAK3 inhibitors (e.g. tofacitinib or R348);
  Syk inhibitors and prodrugs thereof (e.g. fostamatinib and R-406);
  Phosphodiesterase-4 inhibitors (e.g. tetomilast);
  HMPL-004;
  probiotics;
  Dersalazine;
  semapimod/CPSI-2364; and
  protein kinase C inhibitors (e.g. AEB-071).

For the treatment of eye disorders (such as keratoconjunctivitis sicca or uveitis), possible combinations include combinations with, for example, one or more agents selected from the list comprising:

corticosteroids (e.g. dexamethasone, prednisolone, triamcinolone acetonide, difluprednate or fluocinolone acetonide);
  immunosuppressants (e.g. cyclosporin, voclosporin, azathioprine, methotrexate, mycophenolate mofetil or tacrolimus);
  anti-TNFα antibodies (e.g. infliximab, adalimumab, certolizumab pegol, ESBA-105 or golimumab);
  anti-IL-17A antibodies (e.g. secukinumab);
  mTOR inhibitors (e.g. sirolimus);
  VGX-1027;
  JAK3 inhibitors (e.g. tofacitinib or R348); and
  protein kinase C inhibitors (e.g. AEB-071).

Hence another aspect of the invention provides a compound of formula (I) in combination with one or more further active ingredients, for example one or more active ingredients described above.

Similarly, another aspect of the invention provides a combination product comprising:

(A) a compound of the present invention; and
  (B) one or more other therapeutic agents, wherein each of components (A) and (B) is formulated in admixture with a pharmaceutically-acceptable adjuvant, diluent or carrier.

In this aspect of the invention, the combination product may be either a single (combination) pharmaceutical formulation or a kit of parts.

Thus, this aspect of the invention encompasses a pharmaceutical formulation including a compound of the present invention and another therapeutic agent, in admixture with a pharmaceutically acceptable adjuvant, diluent or carrier (which formulation is hereinafter referred to as a "combined preparation").

It also encompasses a kit of parts comprising components:

(i) a pharmaceutical formulation including a compound of the present invention in admixture with a pharmaceutically acceptable adjuvant, diluent or carrier; and
  (ii) a pharmaceutical formulation including one or more other therapeutic agents, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

The one or more other therapeutic agents (i.e. component (B) above) may be, for example, any of the agents mentioned above in connection with the treatment of respiratory, gastrointestinal and eye disorders.

If component (B) is more than one further therapeutic agent, these further therapeutic agents can be formulated with each other or formulated with component (A) or they may be formulated separately.

In one embodiment component (B) is one other therapeutic agent. In another embodiment component (B) is two other therapeutic agents.

The combination product (either a combined preparation or kit of parts) of this aspect of the invention may be used in the treatment or prevention of an inflammatory disease e.g. the inflammatory diseases mentioned above, such as:
  respiratory disorders including COPD (including chronic bronchitis and emphysema), asthma, paediatric asthma, cystic fibrosis, sarcoidosis, idiopathic pulmonary fibrosis, allergic rhinitis, rhinitis and sinusitis, especially asthma, or COPD (including chronic bronchitis and emphysema);
  eye diseases or disorders including allergic conjunctivitis, conjunctivitis, keratoconjunctivitis sicca (dry eye), glaucoma, diabetic retinopathy, macular oedema (including diabetic macular oedema), central retinal vein occlusion (CRVO), dry and/or wet age related macular degeneration (AMD), post-operative cataract inflammation or, particularly, uveitis (including posterior, anterior and pan uveitis), corneal graft and limbal cell transplant rejection;
  skin diseases or disorders including allergic dermatitis, contact dermatitis, atopic dermatitis or psoriasis; and
  gastrointestinal diseases or disorders including gluten sensitive enteropathy (coeliac disease), eosinophilic esophagitis, intestinal graft versus host disease or, particularly, ulcerative colitis or Crohn's disease.

The aspects of the invention described herein (e.g. the above-mentioned compound, combinations, methods and uses) may have the advantage that, in the treatment of the conditions described herein, they may be more convenient for the physician and/or patient than, be more efficacious than, be less toxic than, be longer acting than, have better selectivity over, have a broader range of activity than, be more potent than, produce fewer side effects than, have a better pharmacokinetic and/or pharmacodynamic profile than, have more suitable solid state properties than, have better stability than, or may have other useful pharmacological properties over, similar compounds, combinations, methods (treatments) or uses known in the prior art for use in the treatment of those conditions or otherwise.

Relative to compounds of the prior art, in at least some embodiments the compound of formula (I) is expected to have one or more of the following attributes:
  it exhibits properties that are particularly suited to topical/local administration (e.g. following topical/local administration, the generation of high target tissue concentrations but low plasma or systemic concentrations of the compound of formula (I) and/or rapid clearance of the compound of formula (I) from plasma or the systemic circulation);
  it has a reduced risk of extravascular exposure following intravenous administration (e.g. due to a low volume of distribution for the compound of formula (I)); it exhibits its superior potency with respect to selected kinases and/or a panel of kinases, such as p38 MAPKα, p38 MAPKγ, Src and p59-HCK;
  it exhibits low or no inhibitory activity against Olaharsky kinases, particularly GSK3a;
  it exhibits low or no inhibitory activity against Syk kinase;
  it exhibits reduced β-catenin induction and/or inhibition of mitosis in cells;
  it exhibits no or less time-dependent inhibition of members of the cytochrome P450 superfamily; and/or
  it produces less problematic (e.g. less toxic) metabolites, e.g. following administration to a patient.

Experimental Section

Abbreviations used herein are defined below (Table 1). Any abbreviations not defined are intended to convey their generally accepted meaning.

Table 1: Abbreviations

AcOH glacial acetic acid
Ac$_2$O acetic anhydride
Aq aqueous
b broad
BEH ethylene bridged hybrid
BINAP 1,1'-binaphthyl-2,2'-diamine
Boc tert-butoxycarbonyl
CSH charged surface hybrid
d doublet
Δ chemical shift
DCM dichloromethane
DIAD diisopropyl azodicarboxylate
DMF N,N-dimethylformamide
DMSO dimethyl sulfoxide
(ES$^+$) electrospray ionization, positive mode
(ES$^-$) electrospray ionization, negative mode
Et ethyl
EtOAc ethyl acetate
EtOH ethanol
h hour(s)
1-[bis(dimethylamino)methylene]-1H-1,2,3-triazolo[4,5-b]pyridinium 3-HATU oxid hexafluorophosphate
Hunig's base N, N-diisopropylethylamine
IPA isopropyl alcohol
$^i$PrOAc isopropyl acetate
m multiplet
(M+H)$^+$ protonated molecular ion
(M−H)$^-$ deprotonated molecular ion
Me methyl
MeCN acetonitrile
MeOH methanol
MHz megahertz
min minute(s)
m/z mass-to-charge ratio
NMR nuclear magnetic resonance (spectroscopy)
Pd$_2$(dba)$_3$ tris(dibenzylideneacetone)dipalladium(0)
Ph phenyl
q quartet
RT room temperature
HPLC high performance liquid chromatography
s singlet
Sat saturated
SCX solid supported cation exchange (resin)
t triplet
$^t$Bu tent-butyl
THF tetrahydrofuran
TFA trifluoroacetic acid
UV ultra-violet
AKT v-akt murine thymoma viral oncogene homolog 1

ATP adenosine-5'-triphosphate
BALF bronchoalveolar lavage fluid
BSA bovine serum albumin
COPD chronic obstructive pulmonary disease
CXCL1 chemokine (C-X-C motif) ligand 1
COX2 cytochrome c oxidase subunit II
DSC differential scanning calorimetry
DSS dextran sodium sulfate
DTT dithiothreitol
d-U937 cells PMA differentiated U-937 cells
DVS dynamic vapour sorption
dsRNA double stranded RNA
ELISA enzyme-linked immunosorbent assay
FACS fluorescence-activated cell sorting
FBS foetal bovine serum
FRET fluorescence resonance energy transfer
GM-CSF CSF2: granulocyte-macrophage colony-stimulating factor
GSK3α glycogen synthase kinase 3α
GSK3β glycogen synthase kinase 3β
HBSS Hank's balanced salt solution
HCK hemopoietic cell kinase
HRV human rhinovirus
IBD inflammatory bowel disease
$IC_{50}$ 50% Inhibitory concentration
ICAM-1 inter-cellular adhesion molecule 1
IFN interferon
IL-2 interleukin 2
IL-8 interleukin 8
JNK c-Jun N-terminal kinase
KC keratinocyte chemoattractant
LPMC lamina propria mononuclear cell
LPS lipopolysaccharide
MAPK mitogen-activated protein kinase
MAPKAP-K2 mitogen-activated protein kinase-activated protein kinase-2
MKK4 mitogen-activated protein kinase kinase 4
MKK6 mitogen-activated protein kinase kinase 6
MOI multiplicity of infection
MTT 3-(4,5-dimethylthiazol-2-yl)-2,5-diphenyltetrazolium bromide
OD optical density
PBMC peripheral blood mononuclear cell
PBS Dulbecco's phosphate buffered saline
PHA phytohaemagglutinin
PI3 phosphoinositide 3 kinase
PMA phorbol 12-myristate 13-acetate
REC50 relative 50% effective concentration
RNA ribonucleic acid
RNAi RNA interference
RSV respiratory syncytical virus
SDS sodium dodecyl sulphate
SMS surface measurements systems
SRC v-src sarcoma (Schmidt-Ruppin A-2) viral oncogene homolog (avian)
Syk spleen tyrosine kinase
TCID50 50% tissue culture infectious dose
TGA thermogravimetric analysis
TLR3 toll-like receptor 3
TNBS 2,4,6-trinitrobenzenesulphonic acid
TNFα tumor necrosis factor alpha
URTI upper respiratory tract infection
XPD powder X-ray diffraction
XRD X-ray diffraction Chemistry Examples General Procedures All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 µm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M $NH_3$ in MeOH.

Preparative Reverse Phase High Performance Liquid Chromatography

Performed using UV detection at 215 and 254 nm with either a Waters X-Select Prep-C18, 5 µm, 19×50 mm column eluting with a $H_2O$-MeCN gradient containing 0.1% v/v formic acid over 10 min, or a Waters X-Bridge Prep-C18, 5 µm, 19×50 mm column eluting with a $H_2O$-MeCN gradient containing 0.1% ammonium bicarbonate over 10 min.

Analytical Methods

Reverse Phase High Performance Liquid Chromatography

Method 1: Waters XSelect CSH C18 2.5 µm (4.6×30 mm) at 40° C.; flow rate 2.5-4.5 mL $min^{-1}$ eluted with a $H_2O$-MeCN gradient containing 0.1% v/v formic acid over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL $min^{-1}$; 3.01-3.50 min, held at 5% $H_2O$-95% MeCN; 3.50-3.60 min, returned to 95% $H_2O$-5% MeCN, flow rate reduced to 3.50 mL $min^{-1}$; 3.60-3.90 min, held at 95% $H_2O$-5% MeCN; 3.90-4.00 min, held at 95% $H_2O$-5% MeCN, flow rate reduced to 2.5 mL $min^{-1}$.

Method 2: Waters XBridge BEH C18, 2.5 µm (4.6×30 mm) at 40° C.; flow rate 2.5-4.5 mL $min^{-1}$ eluted with a $H_2O$-MeCN gradient containing 10 mM ammonium bicarbonate over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL $min^{-1}$; 3.01-3.50 min, held at 5% $H_2O$-95% MeCN; 3.50-3.60 min, returned to 95% $H_2O$-5% MeCN, flow rate reduced to 3.50 mL $min^{-1}$; 3.60-3.90 min, held at 95% $H_2O$-5% MeCN; 3.90-4.00 min, held at 95% $H_2O$-5% MeCN, flow rate reduced to 2.5 mL $min^{-1}$.

$^1$H NMR Spectroscopy $^1$H NMR spectra were acquired on a Bruker Avance III spectrometer at 400 MHz using residual undeuterated solvent as reference and unless specified otherwise were run in DMSO-$d_6$.

EXAMPLES

Example 1A 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea Intermediate A:
3-tert-Butyl-1-p-tolyl-1H-pyrazol-5-amine

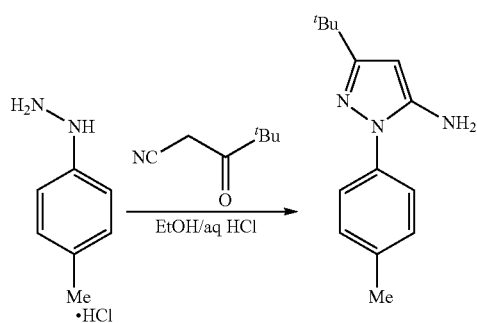

To a stirred solution of p-tolylhydrazine hydrochloride (100 g, 630 mmol) in EtOH (1251 mL) was added 4,4-dimethyl-3-oxopentanenitrile (88 g, 699 mmol) and HCl (62.5 mL, 750 mmol). The resulting mixture was stirred at reflux overnight. The reaction mixture was cooled to room temperature and concentrated in vacuo to c.a. ⅓ of the original volume. The reaction mixture was then cooled in an ice-bath and taken to c.a. pH 8-9 with 6M aq NaOH. The reaction mixture was extracted with diethyl ether (500 mL) and the organic phase washed with water (2×300 mL) before being dried over magnesium sulphate and concentrated in vacuo to afford an orange solid. The solid was suspended in iso-hexane and stirred at reflux for 2.5 h before being cooled and filtered whilst still hot to yield the subtitle product 3-tert-butyl-1-p-tolyl-1H-pyrazol-5-amine as a pale brown solid (76.5 g, 52%); R$^t$ 1.31 min (Method 1); m/z 230 (M+H)$^+$(ES$^+$); $^1$H NMR δ: 1.20 (9H, s), 2.32 (3H, s), 5.10 (2H, br s), 5.35 (1H, s), 7.24 (2H, d), 7.42 (2H, m).

Intermediate B: Phenyl (3-(tert-butyl)-1-(p-tolyl)-1H-pyrazol-5-yl)carbamate

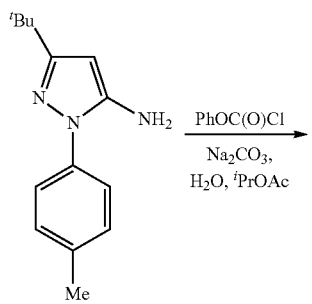

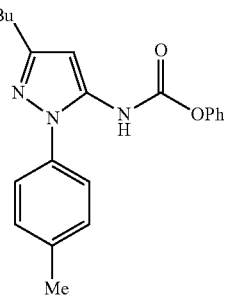

A solution of 3-(tert-butyl)-1-(p-tolyl)-1H-pyrazol-5-amine (Intermediate A) (20 g, 87.0 mmol) in isopropyl acetate (240 mL) was added to a stirred solution of sodium carbonate (11.3 g, 106 mmol) in water (80 mL). After 10 min phenyl chloroformate (12.1 mL, 96 mmol) was added and the resulting mixture was stirred at ambient temperature overnight. The reaction mixture was diluted with water (160 mL), the layers were separated and the organics were washed with water (2×80 mL), brine (80 mL), dried (MgSO$_4$) and concentrated in vacuo. The resulting yellow solid was suspended in 10% ether/iso-hexane (320 mL) and stirred until a uniform suspension was obtained. The solid was collected by filtration and washed with iso-hexane to yield the subtitle compound phenyl (3-(tert-butyl)-1-(p-tolyl)-1H-pyrazol-5-yl)carbamate as a white powder (27.3 g, 88%); R$^t$ 2.65 min (Method 1); m/z 350 (M+H)$^+$ (ES$^+$); $^1$H NMR δ:1.29 (9H, s), 2.37 (3H, s), 6.35 (1H, s), 7.10-7.23 (3H, overlapping m), 7.33-7.46 (6H, overlapping m), 9.99 (1H, s).

Intermediate C: tert-Butyl (4-((2-chloropyridin-4-yl)methoxy)naphthalen-1-yl)carbamate

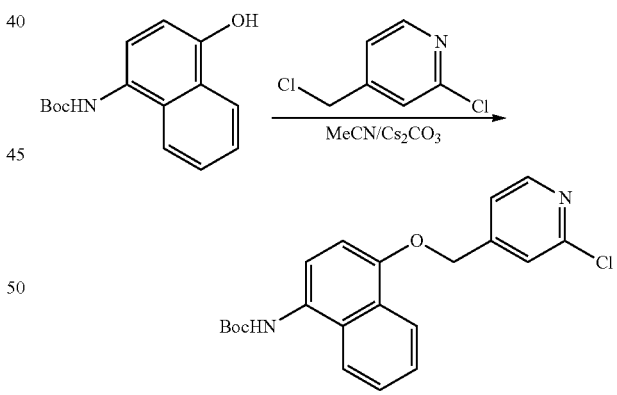

To a mixture of 2-chloro-4-(chloromethyl)pyridine (30 g, 185 mmol) and tert-butyl (4-hydroxynaphthalen-1-yl)carbamate (40.0 g, 154 mmol) in acetonitrile (200 mL) was added caesium carbonate (75 g, 231 mmol) and the resulting mixture was heated to 55° C. After 16 h the reaction mixture was diluted with 30% MeOH in DCM (600 mL) and water (400 mL). The layers were separated and the aqueous layer was extracted with a further amount of 30% MeOH in DCM (2×600 mL) and the organics were concentrated in vacuo to afford the crude product. The crude product was triturated with MeOH (200 mL), sonicated for c.a. 5 min and slurried for 1 day. The resulting solid was collected by filtration and washed with MeOH (2×10 mL) to yield the subtitle compound tert-butyl (4-((2-chloropyridin-4-yl)methoxy)naphthalen-1-yl)carbamate as a yellow solid (43 g, 70%); R$^t$ 2.60 min (Method 1); m/z 383 (M−H)$^−$ (ES$^−$); $^1$H NMR δ:1.47 (9H, s), 5.41 (2H, s), 6.98 (1H, d), 7.36 (1H, d), 7.55-7.61 (3H, overlapping m), 7.65 (1H, m), 7.94 (1H, m), 8.29 (1H, m), 8.45 (1H, m), 9.00 (1H, bs).

Intermediate D (protected): tert-Butyl (4-((2-((6-ethylpyrazin-2-yl)amino)pyridin-4-yl)methoxy)naphthalen-1-yl)carbamate

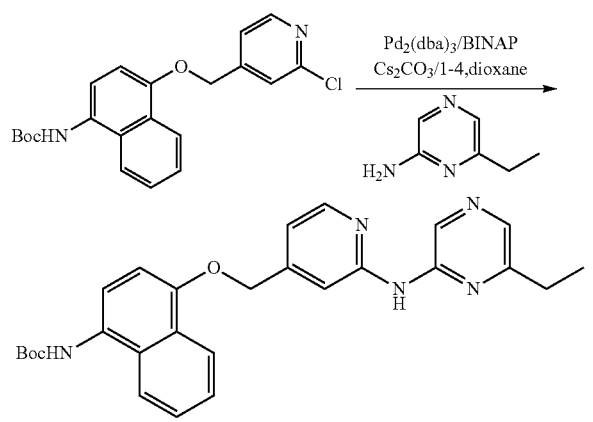

A mixture of tert-butyl (4-((2-chloropyridin-4-yl)methoxy)naphthalen-1-yl)carbamate (Intermediate C) (1050 mg, 2.73 mmol), 6-ethylpyrazin-2-amine (437 mg, 3.55 mmol), and cesium carbonate (1333 mg, 4.09 mmol) in 1,4-dioxane (15 mL) was degassed with nitrogen for 5 min. A solution of Pd$_2$(dba)$_3$ (125 mg, 0.136 mmol) and BINAP (170 mg, 0.273 mmol) in 1,4-dioxane (5 mL) was added, and the reaction mixture stirred at 90° C. for 6 h. The reaction mixture was allowed to cool and was stirred at room temperature for 16 h, then diluted with 10% MeOH/DCM (25 mL) and filtered through a plug of Celite, washing with additional 10% MeOH/DCM (15 mL). The solvent was removed in vacuo and the crude product was combined with MeOH (15 mL) and slurried for 3 h. The resulting orange solid was isolated by filtration, then combined with MeOH/EtOH (5 mL) solution and stirred for 72 h. Again the resulting orange solid was isolated by filtration, then acetone (20 mL) was added and the mixture was slurried for 2 h. The residual solid was filtered off, and the filtrate was evaporated to give the subtitle compound tert-butyl (4-((2-((6-ethylpyrazin-2-yl)amino)pyridin-4-yl)methoxy)naphthalen-1-yl)carbamate (360 mg, 27%); R$^t$ 2.6 min (Method 2); m/z 472 (M+H)$^+$(ES$^+$); $^1$H NMR δ: 1.18 (3H, t), 1.47 (9H, s), 2.63 (2H, q), 5.36 (2H, s), 6.99 (1H, d), 7.06 (1H, d), 7.36 (1H, d), 7.53-7.63 (2H, m), 7.90-8.06 (3H, overlapping m), 8.29 (1H, d), 8.36 (1H, m), 8.91 (1H, s), 8.96 (1H, s), 10.06 (1H, s).

Intermediate D: N-(4-(((4-aminonaphthalen-1-yl)oxy)methyl)pyridin-2-yl)-6-ethylpyrazin-2-amine

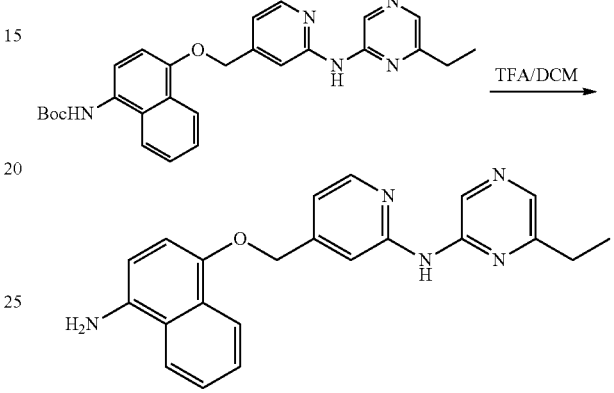

TFA (1.485 mL, 19.09 mmol) was added to a solution of tert-butyl (4-((2-((6-ethylpyrazin-2-yl)amino)pyridin-4-yl)methoxy)naphthalen-1-yl)carbamate (Intermediate D (protected)) (360 mg, 0.763 mmol) in DCM (15 mL), and the reaction mixture stirred at room temperature for 4 h, then concentrated in vacuo. The residue was combined with sat. sodium hydrogencarbonate solution and stirred at room temperature for 16 h. The solid was filtered, washing with acetonitrile, and dried under vacuum to give the subtitle compound N-(4-(((4-aminonaphthalen-1-yl)oxy)methyl)pyridin-2-yl)-6-ethylpyrazin-2-amine as a beige solid (200 mg, 69%); R$^t$ 2.14 min (Method 2); m/z 372 (M+H)$^+$(ES$^+$); $^1$H NMR δ: 1.20 (3H, t), 2.64 (2H, q), 5.18-5.24 (4H, overlapping m), 6.59 (1H, d), 6.82 (1H, d), 7.03 (1H, d), 7.41-7.51 (2H, overlapping m), 7.98-8.01 (2H, m), 8.04 (1H, m), 8.22-8.29 (2H, overlapping m), 8.91 (1H, s), 10.04 (1H, s).

1-(3-(tert-Butyl)-1-(p-tolyl)-1H-pyrazol-5-yl)-3-(4-((2-((6-ethylpyrazin-2-yl)amino)pyridin-4-yl)methoxy)naphthalen-1-yl)urea

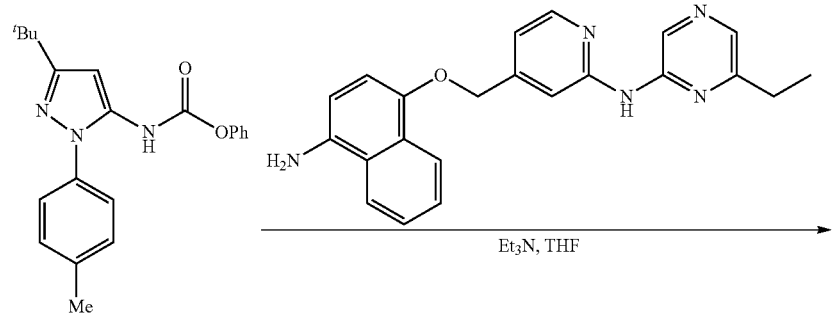

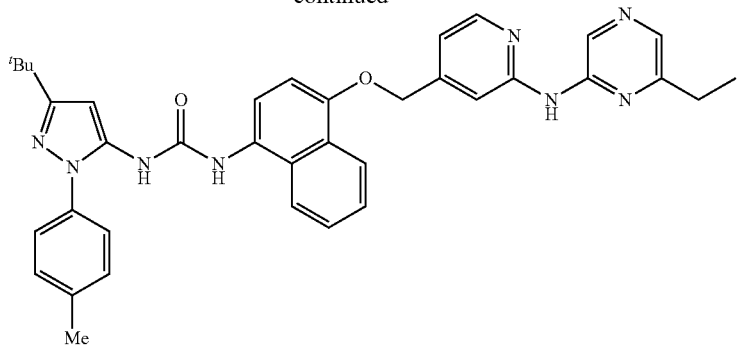

Triethylamine (0.013 mL, 0.093 mmol) was added to a solution of phenyl (3-(tert-butyl)-1-(p-tolyl)-1H-pyrazol-5-yl)carbamate (Intermediate B) (0.042 g, 0.121 mmol) and N-(4-(((4-aminonaphthalen-1-yl)oxy)methyl)pyridin-2-yl)-6-ethylpyrazin-2-am ine (Intermediate D) (0.093 g, 0.250 mmol) in THF (1.5 mL) at 40° C. The reaction mixture was stirred at 40° C. for 40 min then cooled to RT and stirred for 3 days, and then concentrated in vacuo. The crude product was purified by silica gel chromatography (12 g column, 0 to 5% MeOH in DCM) to give an off white-brown solid. The product was re-purified by preparative HPLC (Gilson, Acidic (0.1% Formic acid), Acidic, Waters X-Select Prep-C18, 5 µm, 19×50 mm column, 45-75% MeCN in Water) to afford the title compound 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea as an off white solid (0.029 g, 49%); R$^t$ 2.26 min (Method 1); m/z 627 (M+H)$^+$ (ES$^+$), 625 (M−H)$^-$(ES$^-$); $^1$H NMR δ: 1.18 (3H, t), 1.28 (9H, s), 2.40 (3H, s), 2.63 (2H, q), 5.36 (2H, s), 6.36 (1H, s), 7.02 (1H, d), 7.07 (1H, dd), 7.37 (2H, m), 7.45 (2H, m), 7.56-7.67 (3H, overlapping m), 7.94 (1H, m), 7.99 (1H, s), 8.02 (1H, s), 8.30 (1H, d), 8.39 (1H, m), 8.60 (1H, s), 8.81 (1H, s), 8.92 (1H, s), 10.08 (1H, s).

Example 1B 1-(3-(tert-butyl)-1-(p-tolyl)-1 H-pyrazol-5-yl)-3-(4-((2-((6-ethylpyrazin-2-yl)amino)pyridin-4-yl)methoxy)naphthalen-1-yl)urea (different batch)

1-(3-(tert-Butyl)-1-(p-tolyl)-1H-pyrazol-5-yl)-3-(4-((2-((6-ethylpyrazin-2-yl)amino)pyridin-4-yl)methoxy)naphthalen-1-yl)urea (10.0 g) was stirred in acetonitrile (770 mL) at 22° C. The heterogeneous mixture was warmed to reflux temperature at a rate of 3° C./min and reflux was maintained for 2.5 h. The mixture was seeded with crystalline 1-(3-(tert-butyl)-1-(p-tolyl)-1 H-pyrazol-5-yl)-3-(4-((2-((6-ethylpyrazin-2-yl)am ino)pyridin-4-yl)methoxy)naphthalen-1-yl)urea (100 mg). The mixture was linearly cooled to 20° C. over 18 h then again heated to reflux temperature and refluxed for 2 h then linearly cooled to 22° C. over 18 h. The solid product was filtered, washed with acetonitrile (77 mL) and dried for 18 h at 45° C. in vacuo to give 1-(3-(tert-butyl)-1-(p-tolyl)-1H-pyrazol-5-yl)-3-(4-((2-((6-ethyl-pyrazin-2-yl)amino) pyridin-4-yl)methoxy)naphthalen-1-yl)urea (8.73 g).

Example 2A 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 2)

Intermediate C: tert-Butyl (4-((2-chloropyridin-4-yl)methoxy)naphthalen-1-yl)carbamate

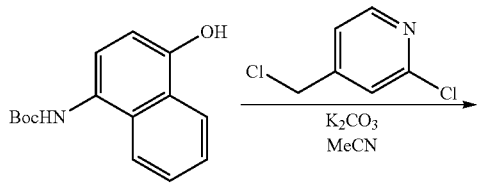

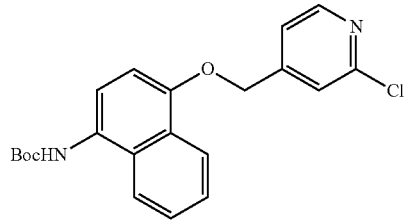

Acetonitrile (420 mL) was added to 2-chloro-4-(chloromethyl)pyridine (1.05 eq, 59.5 g), and the mixture stirred at 20° C. tert-Butyl (4-hydroxynaphthalen-1-yl)carbamate (90.8 g) was added to the mixture then potassium carbonate (72.6 g) was added. The heterogeneous mixture was warmed to 55° C. at a rate of 1.0 K/min.

The mixture was stirred for 16 h at 55° C. then the reaction mixture was cooled to 22° C. Water (1260 mL) was added over 30 min and the mixture was stirred for 30 min at 22° C. The precipitate was filtered and washed twice with 200 mL water. The product was dried in vacuo at 50° C. for 20 h to give tert-butyl (4-((2-chloropyridin-4-yl)methoxy)naphthalen-1-yl)carbamate (100.0 g, 90.6%).

Intermediate D (protected): tert-Butyl (4-((2-((6-ethylpyrazin-2-yl)amino)pyridin-4-yl)methoxy)naphthalen-1-yl)carbamate

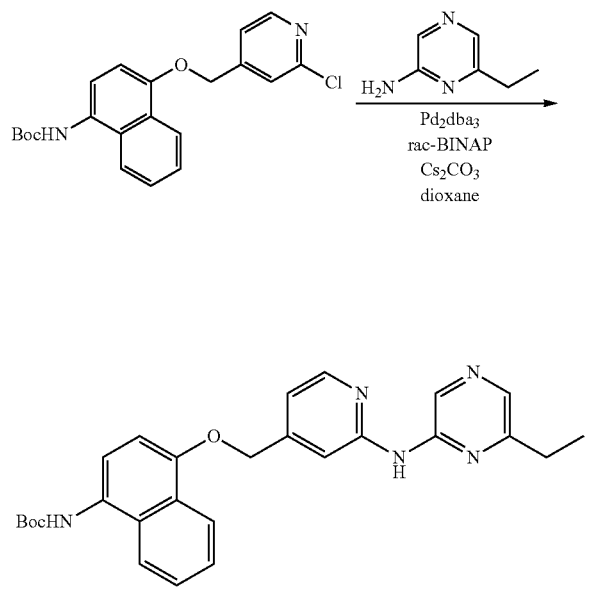

Dioxane (125 mL) was added to tert-butyl (4-((2-chloropyridin-4-yl)methoxy)naphthalen-1-yl)carbamate (Intermediate C) (9.6 g) and the mixture stirred at 20° C. Cesium carbonate (2 eq, 16.3 g) and 2-amino-6-ethylpyrazine (1.5 eq, 4.8 g) were added to the stirred mixture at 20° C. Argon was purged through the reaction mixture.
Tris(dibenzylideneacetone)dipalladium(0) (0.05 eq, 1.14 g) and racemic BINAP (0.10 eq, 1.56 g) were added to the reaction mixture. The mixture was stirred for an additional 15 min at 20° C. The mixture was heated to 90° C. at a rate of 1.5 K/min then stirred for 12 h at 90° C. The mixture was cooled to 20° C. and stirring continued for an additional 6 h. The heterogeneous mixture was filtered over Celite, and the filter washed with dioxane (twice 5 mL). The filtrate was concentrated in vacuo at 20 mbar and 50° C. The residue was dissolved in ethanol (150 mL). Spontaneous crystallization occurred. The heterogeneous mixture was stirred for 3 h at 22° C. The precipitate was filtered and washed with ethanol (10 mL). The product was dried in vacuo at 50° C. for 20 h to give tert-butyl (4-((2-((6-ethylpyrazin-2-yl)amino)pyridin-4-Amethoxy)naphthalen-1-yl)carbamate (9.05 g, 76.8%).

Intermediate D: N-(4-(((4-aminonaphthalen-1-yl)oxy)methyl)pyridin-2-yl)-6-ethylpyrazin-2-amine

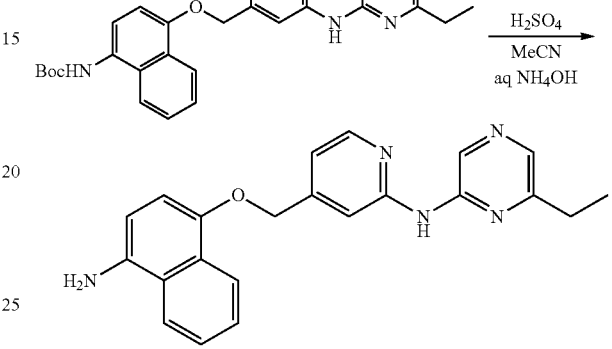

Acetonitrile (200 mL) was added to tert-butyl (4-((2-((6-ethylpyrazin-2-yl)amino)pyridin-4-yl)methoxy)naphthalen-1-yl)carbamate (Intermediate D (protected)) (10.5 g) and the heterogeneous mixture was stirred at 20° C. Sulfuric acid (4.5 eq, 5.5 mL) was added over 2 h at 20° C. The heterogeneous mixture was stirred for an additional 2 h at 20° C. Aqueous ammonia (10 eq, 17 mL) was added to the reaction mixture over 15 min and the temperature was kept at 20° C. by cooling. Water (33.4 mL) was added to the heterogeneous mixture over 5 min at 20° C. After stirring for 30 min at 20° C., the mixture was cooled to 5° C. and stirred for an additional 2 h at 5° C. The precipitate was filtered and washed with water (33.4 mL) and 2-propanol (18 mL). The product was dried at 50° C. in vacuo for 24 h to give N-(4-(((4-aminonaphthalen-1-yl)oxy)methyl)pyridin-2-yl)-6-ethylpyrazin-2-amine (6.2 g, 75%). 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea

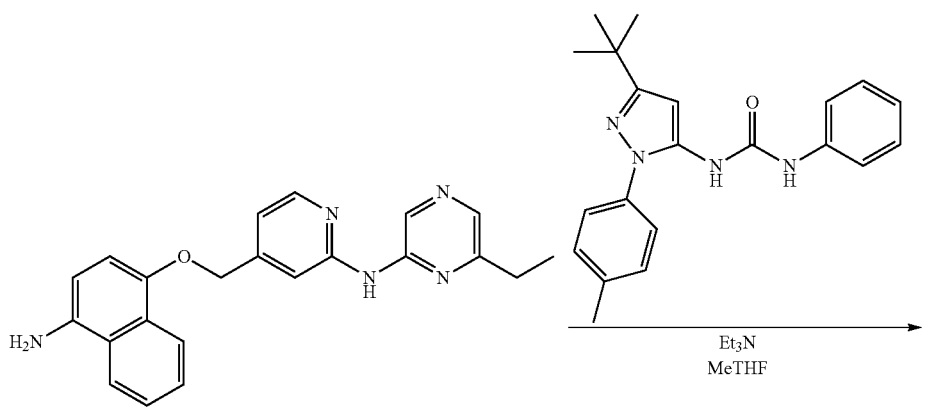

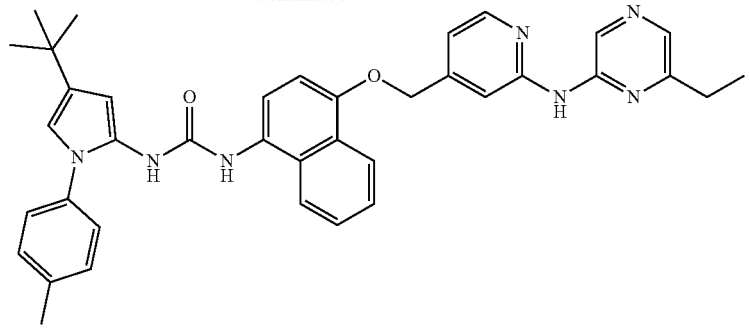

2-methyltetrahydrofuran (1809 mL) was added to N-(4-(((4-aminonaphthalen-1-yl)oxy)methyl)pyridin-2-yl)-6-ethylpyrazin-2-amine (Intermediate D) (41.3 g) and the mixture was stirred at 20° C. Phenyl (3-(tert-butyl)-1-(p-tolyl)-1H-pyrazol-5-yl)carbamate (1.2 eq, 51.3 g) was added to the mixture. Triethylamine (0.25 eq, 3.9 mL) was added and the mixture stirred for an additional 10 min at 20° C. The heterogeneous reaction mixture was warmed to 48° C. over 30 min and kept at 48° C. for 3.5 h. After 10 min at 48° C., the mixture became homogeneous, and was seeded with crystalline 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea (60 mg). The reaction mixture was allowed to cool to 20° C. and stirred for an additional 16 h.

The formed precipitate was filtered and washed with 2-methyltetrahydrofuran (twice 139 mL). The product was dried for 18 h at 45° C. in vacuo to give 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea (54.1 g, 77.5%).

1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 2)

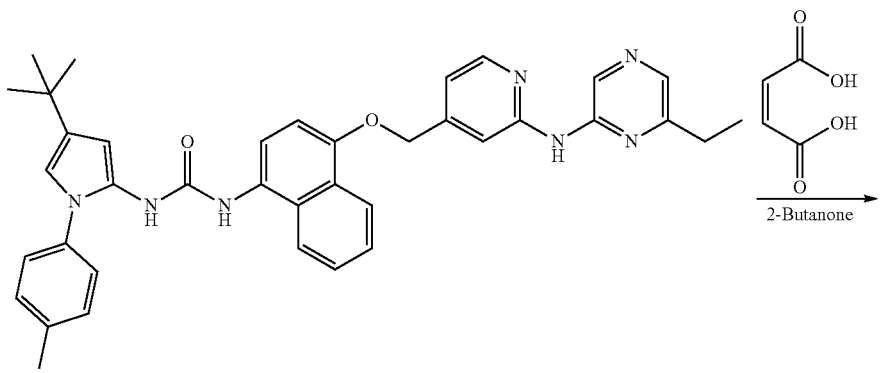

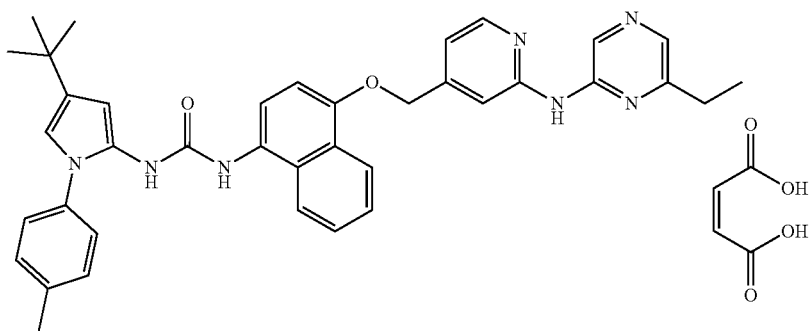

2-Butanone (4442 mL) was added to 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea (111.04 g) and stirred at 20° C. The heterogeneous mixture was warmed to 65° C. and became a homogeneous solution. SilicaMetS Thiol (metal scavenger) (5.55 g) was added and the mixture stirred for 30 min at 65° C. Norit A Supra (activated charcoal) (5.55 g) added and the mixture stirred for an additional 20 min at 65° C. The mixture was filtered warm over Celite. The filter was washed with warm 2-butanone (1555 mL) (60° C.). 2-Butanone (2887 mL) was added to the filtrate and brought to 60° C. while stirring.

Maleic acid (1.0 eq, 20.56 g) was dissolved in 2-butanone (555 mL). The maleic acid solution was added to the 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea solution over 80 min at 65° C. After 10% of the maleic acid solution was added, the mixture was seeded with crystalline 1-(3-(tert-butyl)-1-(p-tolyl)-1 H-pyrazol-5-yl)-3-(4-((2-((6-ethylpyrazin-2-yl)amino)pyridin-4-yl) methoxy) naphthalen-1-yl)urea maleate (Form 2). The mixture was kept stirring for 1 h at 60° C., then cooled non-linearly with an exponent of 2.3 over 6 h to 5° C. The precipitate was filtered and washed twice with 2-butanone (278 mL). The product was dried at 45 cC in vacuo for 20 h to give 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 2) (113.8 g, 86.5%).

Example 2B 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 2) (different batch)

2-Butanone (750 mL) was added to 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea (7.50 g) and the mixture was stirred. The mixture was warmed to 60° C. over 20 min. A solution of maleic acid (1.39 g) in 2-butanone (12 mL) was added to the mixture over 5 min. Spontaneous crystallisation occurred after approximately half of the maleic acid solution was added. The mixture was stirred for 30 min at 60° C. then cooled to 5° C. over 6 h with an exponential ramp (exponent =2.3) then stirred for 30 min at 5° C. then heated to 65° C. over 30 min then stirred for 30 min at 65° C. then cooled to 5° C. over 6 h with an exponential ramp (exponent =2.3) then stirred for 30 min at 5° C. then heated to 65° C. over 30 min then stirred for 30 min at 65° C. then cooled to 5° C. over 6 h with an exponential ramp (exponent =2.3). The product was filtered and washed twice with 2-butanone (50 mL), subsequently dried at 45° C. in vacuo to give 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 2) (7.0 g).

Example 2C 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 1)

1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (15 mg) was dissolved in THF (100 vol.) at 50° C. and temperature cycled between 50° C. and room temperature over 24 h (4 h at each temperature). The solution was then kept in the fridge for 24 h after which the solid material (Form 1) was isolated.

Example 2D 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 1) (different batch)

1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea was dissolved in THF (40 vol.) at 50° C. and 1 eq of maleic acid was added. The sample was left to mature between RT and 50° C. (4 h at each temperature) for 2 days. Solid material (Form 1) was isolated.

Example 3

Micronized Batches

Example 3A 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea in micronized form Micronized 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea was prepared by micronising material from Example 1B in a Hosokawa Alpine Spiral Jet Mill 50 AS (5 cm) micronization device (pressure 1.0 bar) (manual feed). The particle size volume parameters determined by laser diffraction using a Malvern Mastersizer 2000S (dispersion in water/Tween80, 0.1%w/v) are given in the table below:

| Dv10 (micron) | Dv50 (micron) | Dv90 (micron) |
| --- | --- | --- |
| 0.15 | 1.54 | 10.76 |

Example 3B 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yyl)urea maleate Form 2 in micronized form Micronized 1-(3-(tert-butyl)-1-(p-tolyl)-1 H-pyrazol-5-yl)-3-(4-((2-((6-ethylpyrazin-2-yl)amino) pyridin-4-yl)methoxy)naphthalen-1-yl)urea maleate (Form 2) was prepared by micronising material from Example 2B in a Hosokawa Alpine Spiral Jet Mill 50 AS (5 cm) micronization device (pressure 1.0 bar) (manual feed). The particle size volume parameters determined by laser diffraction using a Malvern Mastersizer 2000S (dispersion in water/Tween80, 0.1% w/v) for the input and output material are given in the table below:

|  | Dv10 (micron) | Dv50 (micron) | Dv90 (micron) |
|---|---|---|---|
| Input material (Example 2B) | 3 | 9 | 128 |
| Output material (Example 3B) | 1.21 | 2.18 | 4.00 |

Example 4

Lactose containing compositions containing 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea as free base and maleate (Form 2), suitable for inhalation Compositions were prepared by blending ingredients as follows:

| Example | Active ingredient (Example 3B) (maleate (Form 2), micronised) | Lactose monohydrate* | Magnesium stearate** |
|---|---|---|---|
| 4a | 75 mg | 75 mg | — |
| 4b | 75 mg | — | 75 mg |
| 4c | 75 mg | 35 mg | 35 mg |

| Example | Active ingredient (Example 3A) (free base form, micronised)** | Lactose monohydrate* | Magnesium stearate** |
|---|---|---|---|
| 4d | 10 µg | 25 mg | — |
| 4e | 10 µg | 25 mg | 1% |
| 4f | 100 µg | 25 mg | — |

| Example | Active ingredient (Example 3B) (maleate (Form 2), micronised) | Lactose monohydrate* | Magnesium stearate** |
|---|---|---|---|
| 4g | 10 µg | 25 mg | — |
| 4h | 10 µg | 25 mg | 1% |
| 4i | 100 µg | 25 mg | — |

*Lactohale LH200
**Source: Peter Greven (Grade: Ligamed MF-2V; vegetable grade)

*Lactohale LH200 **Source: Peter Greven (Grade: Ligamed MF-2V; vegetable grade)

Example 5

Characterisation and Stability Testing

Physical Characterisation of the Active Ingredient
Infrared spectrometry (IR)—Micro Attenuated Total Reflectance (microATR)
The samples were analyzed using a suitable microATR accessory.
number of scans: 32
resolution: 1 cm$^{-1}$
wavelength range: 4000 to 400 cm$^{-1}$
apparatus: Thermo Nexus 670 FTIR spectrometer
detector: DTGS with KBr windows
beamsplitter: Ge on KBr
micro ATR accessory: Harrick Split Pea with Si crystal
The IR spectrum of a sample of Example 2A material, shown in FIG. 1, reflects the vibrational modes of the molecular structure of Example 1 as its maleate salt.

Powder XRD
Powder X-ray diffraction (XPD) analysis on the Form 2 material was carried out on a
PANanalytical (Philips) X'PertPRO MPD diffractometer. The instrument is equipped with a
Cu LFF X-ray tube.
The compound was spread on a zero background sample holder.
Instrument parameters:
generator voltage: 45 kV
generator amperage: 40 mA
geometry: Bragg-Brentano
stage: spinner stage
Measurement conditions:
scan mode: continuous
scan range: 3 to 50° 2θ
step size: 0.02²/step
counting time: 30 sec/step
spinner revolution time: 1 sec
radiation type: CuKα
Incident beam path: Diffracted beam path:
program. divergence slit: 15 mm long anti scatter shield:+
Soller slit: 0.04 rad Soller slit: 0.04 rad
beam mask: 15 mm Ni filter: +
anti scatter slit: 1° detector: X'Celerator
beam knife: +
Powder X-ray diffraction (XPD) analysis on the Form 1 material was carried out on a Bruker
AXS C2 GADDS diffractometer. The compound was lightly pressed on a glass slide.
Instrument parameters:
generator voltage: 40 kV
generator amperage: 40 mA
geometry: reflection (=Bragg-Brentano)
stage: automated XYZ stage
Measurement conditions:
scan mode: continuous
scan range: 3 to 30° 2θ
step size: 0.05°/step
counting time: 120 sec
radiation type: CuKα
detector: HiStar 2-dimensional
Single Göbel multilayer mirror coupled with a pinhole collimator of 0.3 mm
The powder XRD pattern of a sample of Example 2A material, shown in FIG. 2, shows diffraction peaks without the presence of a halo, indicating that the compound is present as a crystalline product. This XRD pattern is characteristic of crystalline polymorph Form 2.
The powder XRD pattern of a sample of Example 2D material, shown in FIG. 3, shows diffraction peaks without the presence of a halo, indicating that the compound is present as a crystalline product. This XRD pattern is characteristic of crystalline polymorph Form 1.
Differential Scanning Calorimetry (DSC)
About 3 mg of the test compound was transferred into a standard aluminum TA-Instrument sample pan. The sample pan was closed with the appropriate cover and the DSC curve recorded on a TA-Instruments Q1000 MTDSC equipped with a RCS cooling unit.

Figure 4:
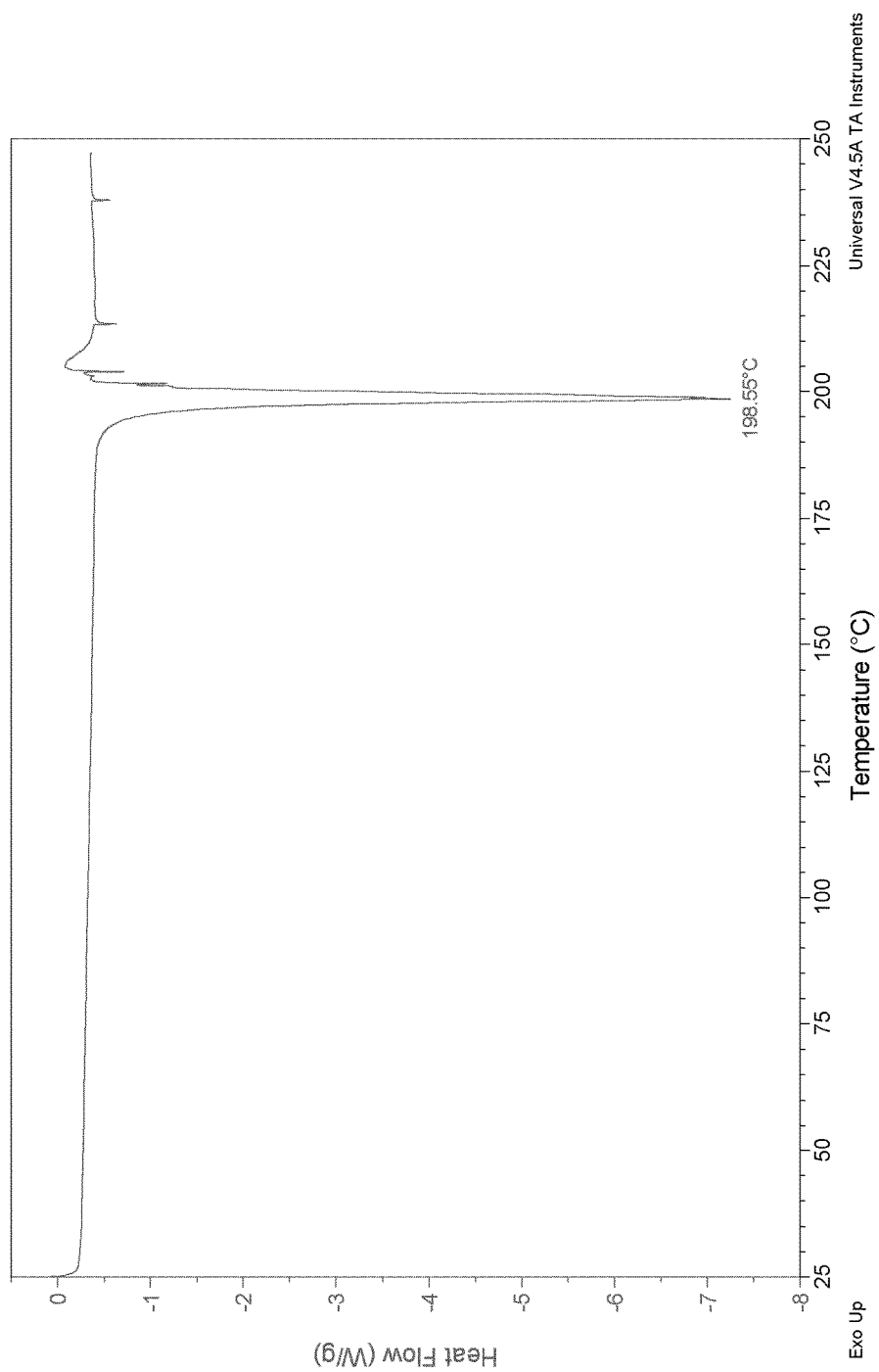
FIG. 4 shows a DSC curve of a sample of the compound of formula (I), maleate salt, Form 2

The following parameters were used:
initial temperature: 25° C.
heating rate: 10° C./min
final temperature: 300° C.
nitrogen flow: 50 mL/min The DSC curve of a sample of Example 2A material, shown in FIG. 4, reveals the melting with decomposition of the product at about 198.6° C. (Form 2).

Thermogravimetric Analysis (TGA)

The test compound was transferred into an aluminum sample pan. The thermogravimetric curve was recorded on a TA Instruments Q500 thermogravimeter. The following parameters were used:
initial temperature: room temperature
heating rate: 20° C./min
resolution Factor: 4
final condition: 300° C. or <80[(w/w) %]

Figure 5:
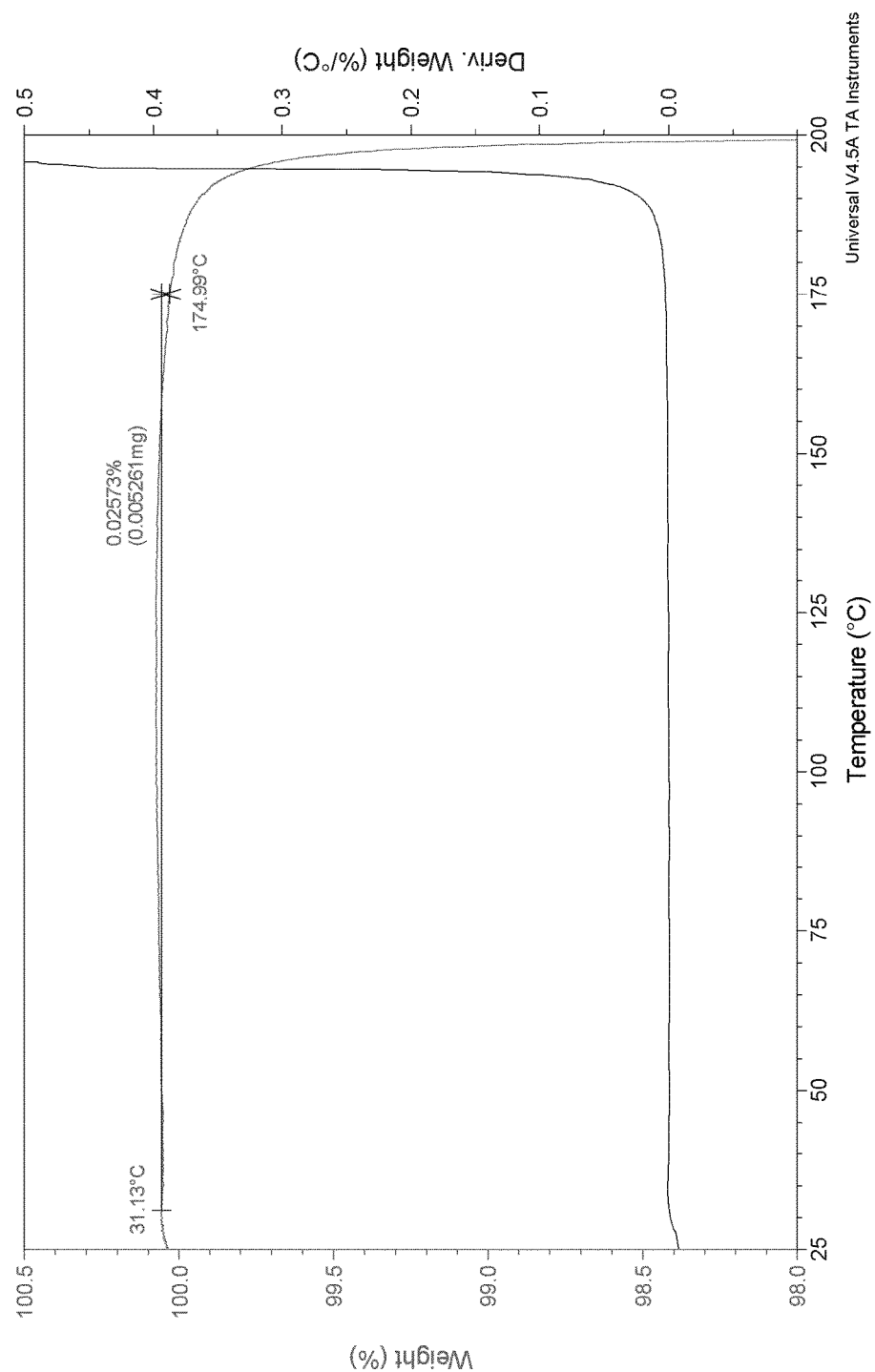
FIG. 5 shows a TGA curve of a sample of the compound of formula (I), maleate salt, Form 2

A TGA plot of a sample of Example 2A material is shown in FIG. 5. No weight loss was registered in the temperature region from room temperature up to 175° C. The weight loss above 175° C. is due to evaporation and decomposition of the product.

Dynamic Vapour Sorption (DVS)

About 20 mg of test compound was transferred into a SMS dynamic vapor sorption and record the weight change with respect to the atmospheric humidity at 25° C.

The following parameters were used:
drying: 60 min. under dry nitrogen
equilibrium: 60 min/Step.
RH (%) measurement points:
first set: 5,10,20,30,40,50,60,70,80,90,95,90,80,70,60,50, 40,30,20,10,5
second set: 10,20,30,40,50,60,70,80,90,95,90,80,70,60, 50,40,30,20,10,5,0

Figure 6:
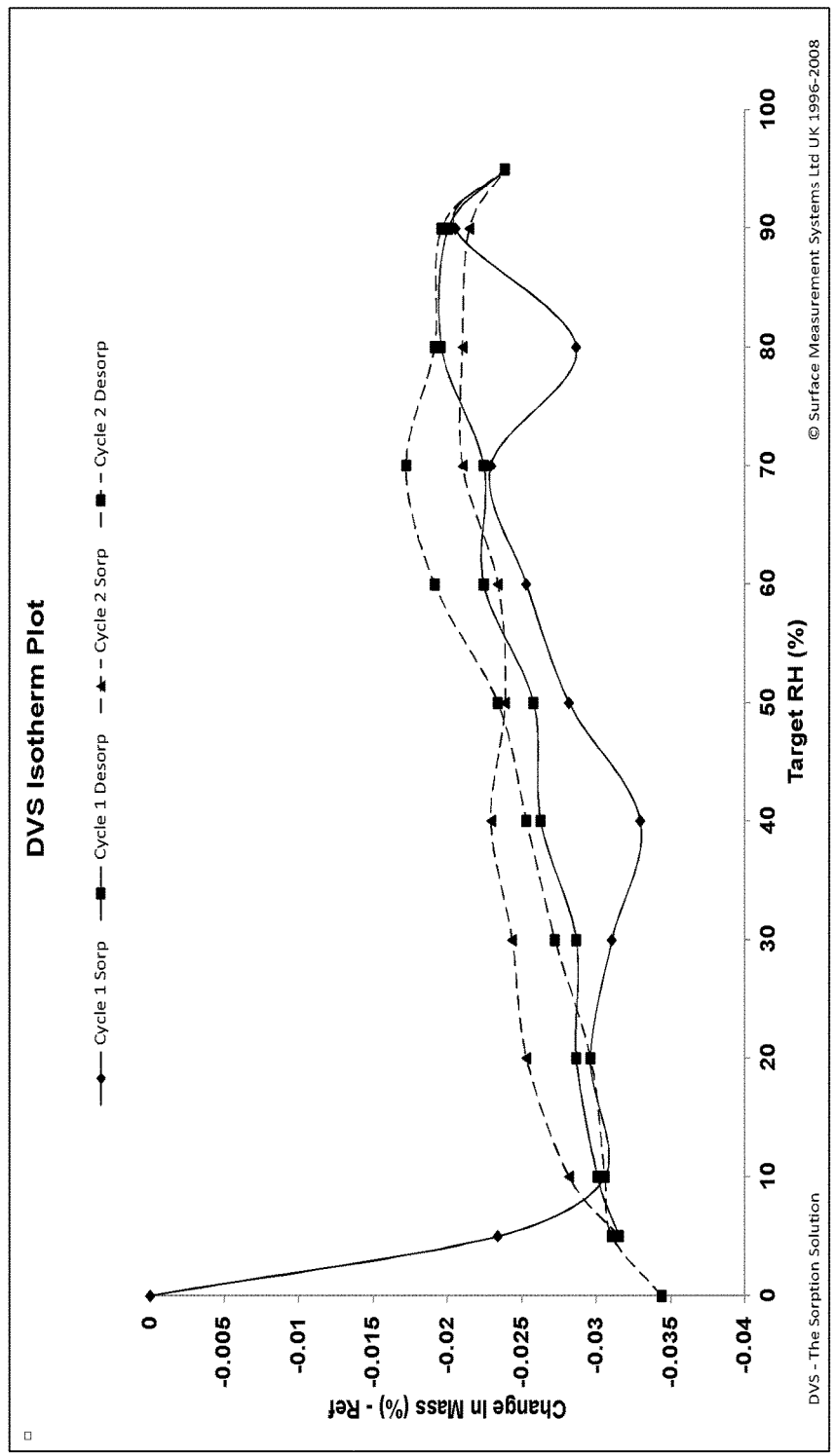
FIG. 6 shows a DVS overlap of a sample of the compound of formula (I), maleate salt, Form 2
Figure 7:
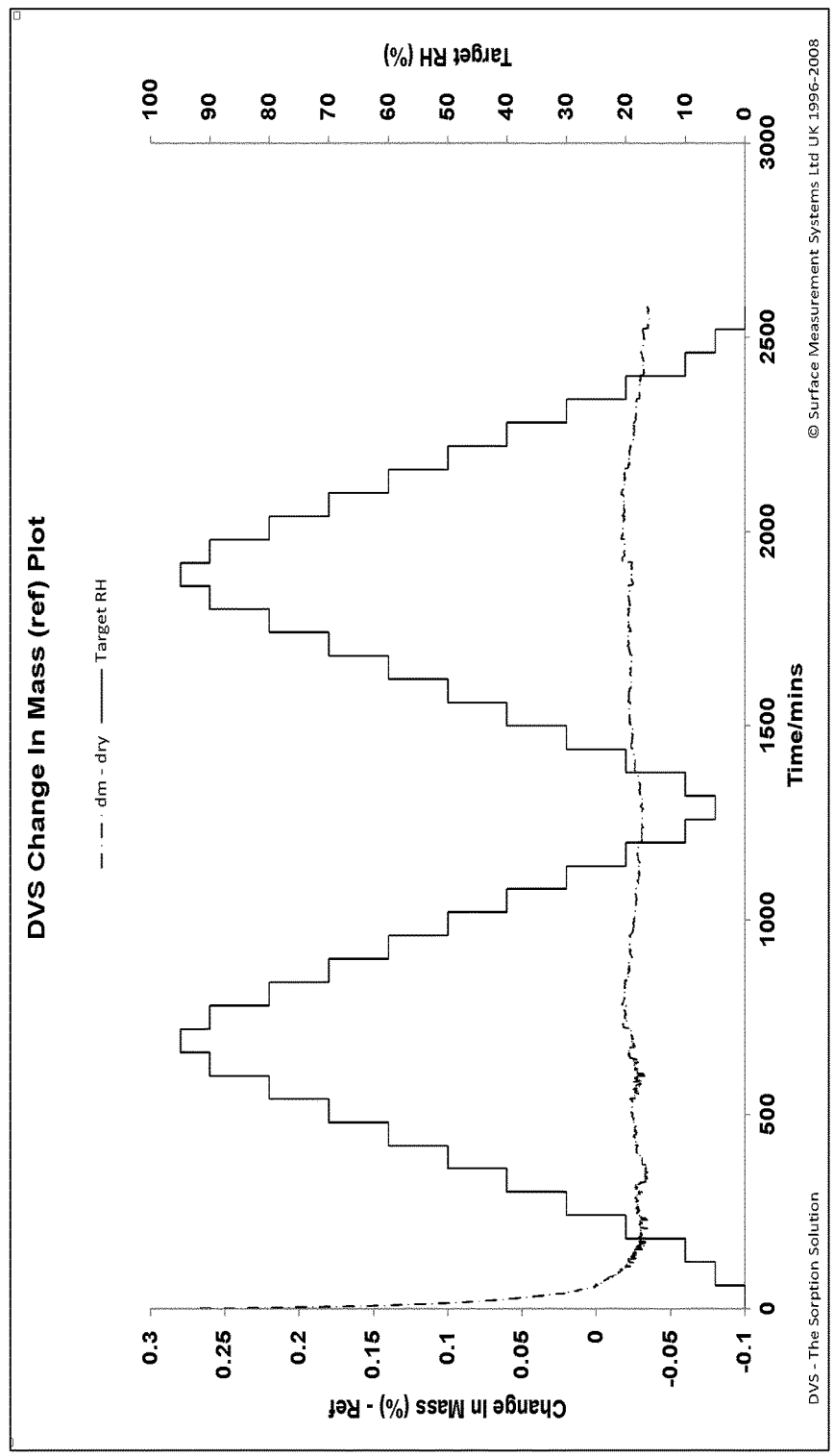
FIG. 7 shows a DVS kinetic plot of a sample of the compound of formula (I), maleate salt, Form 2

DVS testing was performed on a sample of Example 2A material (see FIGS. 6 and 7). During the initial drying step, a weight loss of 0.3% was registered. The product does not appear to be hygroscopic.

The product after DVS, was investigated by XRD and IR and remained in the same solid state form before the test as after the test (data not shown). No indication for dissociation of the salt was observed.

Scanning Electron Microscopy (SEM)

For SEM experiments, data were collected on a Phenom Pro Scanning Electron Microscope. A small quantity of sample was mounted onto an aluminium stub using conducting double-sided adhesive tape. A thin layer of gold was applied using a sputter coater (20 mA, 120 sec).

Samples of Form 1 and Form 2 material of the maleate salt of the compound of the invention were inspected by SEM. Form 1 product had a needle like morphology. Form 2 product had a plate like morphology. The plate like morphology of Form 2 is more suitable for the preparation of an inhaled product than the needle like morphology of Form 1.

Summary of Results of Physical Characterisation of the Active Ingredient

The tested material was crystalline based on XRD and melts with decomposition at around 198.6° C. No weight loss was observed between room temperature and 175° C. by TGA. The material appeared not to be hygroscopic. There was no evidence of solid state conversion or dissociation of the salt. These properties confirm the suitability of the compound of formula (I) maleate salt as a candidate drug.

Physical Characterisation of the Active Ingredient in Micronised Form

A sample of Example 3B material was studied by IR, powder XRD, DSC, TGA and DVS in a similar manner to that described above for Example 2A material. The IR and powder XRD results were substantially the same (data not shown). The tested material was crystalline based on XRD and melts with decomposition at around 194.6° C. according to DSC. The material appeared not to be hygroscopic (data not shown). There was no evidence of solid state conversion or dissociation of the salt (data not shown). These properties confirm the suitability of the compound of formula (I) maleate salt in micronized form as a candidate drug.

Physical Stability Testing—Stability of Lactose Blends

The compositions of Examples 4a, 4b and 4c were stored for 3, 6 and 13 weeks under conditions of 40° C./75% RH, 50° C./80% RH and 50° C./ambient RH. XRD patterns and IR spectra were obtained at time zero and at the three time points (testing parameters were the same as described for characterisation of active ingredient, above). No relevant differences in the XRD patterns or IR spectra were were observed between time zero and any of the time points (data not shown). No solid state form changes or dissociation of the salt was observed.

Chemical stability testing—Stability of Active Ingredient and Blends

UPLC Method for Degradation Determination

Samples were extracted with solvent mixture (DMSO/water 80:20) (7 mL) in a 10 mL vial.

UPLC chromatography was performed using the following parameters:
Column: Supelco Ascentis Express C18, 150 mm length× 3.0 mm i.d., 2.7 μm particle size
Column Temperature: 30° C.
Autosampler Temperature: 5° C.
Flow Rate: 0.40 mL /min
Mobile Phase:
Solvent A: 10 mM ammonium acetate (0.771 g/L) +0.1% v/v trifluoracetic acid in water
Solvent B: acetonitrile/isopropyl alcohol 70:30 (v/v)
Gradient:

| Solvent | Time in minutes | | | | | |
|---|---|---|---|---|---|---|
|  | 0 | 20 | 25 | 30 | 31 | 36 |
| % A | 90 | 35 | 0 | 0 | 90 | 90 |
| % B | 10 | 65 | 100 | 100 | 10 | 10 |

Analysis run time: 36 min
Data collection time: 30 min
Injection volume: 5 μL
Wavelength: scan between 200 and 400 nm
Wavelength used for content uniformity calculations: 334.0 nm The compositions of Examples 4d, 4e, 4f, 4g, 4h and 4i were stored for 14 and 30 days under conditions of 50° C./75% RH, 60° C./30% RH, 60° C./50% RH, 70° C./10% RH, 70° C./75% RH and 80° C./50% RH.

Degradation was measured at time zero and the time points of 7, 14 and 30 days by UPLC and the results are shown in FIG. 8, plates A to F.

The percentage of total degradation for compositions containing the maleate salt, Form 2 of the active ingredient was always lower than that for equivalent compositions containing the free base of the active ingredient indicating that the maleate salt, Form 2 is more stable in these formulations. The percentage of total degradation for compositions containing the maleate salt, Form 2 of the active ingredient at higher concentration was lower than that for compositions containing the maleate salt, Form 2 of the active ingredient at lower concentration in these formulations.

In similar studies on Example 1B and Example 2B material (i.e. unmicronised and unblended material) in which samples were stored for up to 30 days under conditions of 50° C./75% RH, 60° C./50% RH, 70° C./10% RH, 70° C./75% RH and 80° C./50% RH, qualitatively similar results were obtained i.e. the percentage of total degradation for the maleate salt was always lower than that for the free base (data not shown).

From these results it appears that the maleate salt of the compound of the invention is more chemically stable (alone and in combination with lactose) than the free base form.

Example 6

Biological Testing

Experimental Methods for Biological Testing

Enzyme Inhibition Assays

The enzyme inhibitory activities of the compound disclosed herein were determined by FRET using synthetic peptides labelled with both donor and acceptor fluorophores (Z-LYTE, Life Technologies, Paisley, UK).

p38 MAPKα Enzyme Inhibition

The inhibitory activities of the compound of the invention against the p38 MAPKα isoform (MAPK14: Life Technologies), were evaluated indirectly by determining the level of activation/phosphorylation of the target peptide of the p38 MAPKα down-stream molecule, MAPKAP-K2. The enzyme (40 ng/mL, 2.5 µL) was incubated with the test compound (2.5 µL of either 40 µg/mL, 12 µg/mL, 4 µg/mL, 1.2 µg/mL, 0.4 µg/mL, 0.12 µg/mL, 0.04 µg/mL, 0.012 µg/mL, 0.004 µg/mL or 0.0012 µg/mL) for 2 h at RT. The FRET peptides (8 µM, 2.5 µL) and the p38α inactive target MAPKAP-K2 (Life Technologies, 2000 ng/mL), and appropriate ATP solution (2.5 µL, 40 µM) were then added to the enzyme/compound mixture and incubated for 1 h at RT. Development reagent (protease, 5 µL) was added for 1 h prior to detection in a fluorescence microplate reader (EnVision, Perkin Elmer, Waltham, Mass., USA).

p38 MAPKγ Enzyme Inhibition

The inhibitory activities of the compound of the invention against p38MAPKγ (MAPK12: Life Technologies), were evaluated by determining the level of activation/phosphorylation of the target peptide. The enzyme (800 ng/mL, 2.5 µL) was incubated with the test compound (2.5 µL at either 40 µg/mL, 12 µg/mL, 4 µg/mL, 1.2 µg/mL, 0.4 µg/mL, 0.12 µg/mL, 0.04 µg/mL, 0.012 µg/mL, 0.004 µg/mL or 0.0012 µg/mL) for 2 h at RT. The FRET peptides (8 µM, 2.5 µL), and appropriate ATP solution (2.5 µL, 400 µM) were then added to the enzymes/compound mixtures and incubated for 1 h at RT. Development reagent (protease, 5 µL) was added for 1 h prior to detection in a fluorescence microplate reader (EnVision, Perkin Elmer).

Hck, c-Src and Syk Enzyme Inhibition

The inhibitory activities of the compound of the invention against Hck, c-Src and Syk enzymes (Life Technologies) were evaluated in a similar fashion to that described hereinabove. The relevant enzyme (1000 ng/mL, 1400 ng/mL or 2000 ng/mL respectively, 2.5 µL) was incubated with the test compound (either 40 µg/mL, 12 µg/mL, 4 µg/mL, 1.2 µg/mL, 0.4 µg/mL, 0.12 µg/mL, 0.04 µg/mL, 0.012 µg/mL, 0.004 µg/mL or 0.0012 µg/mL, 2.5 µL each) for 2 h at RT. The FRET peptides (8 µM, 2.5 µL), and appropriate ATP solutions (2.5 µL, 800 µM for c-Src, and 60 µM ATP for HCK and Syk) were then added to the enzyme/compound mixtures and incubated for 1 h at RT. Development reagent (protease, 5 µL) was added for 1 h prior to detection in a fluorescence microplate reader (EnVision, Perkin Elmer).

GSK 3α Enzyme Inhibition

The inhibitory activities of the compound of the invention against the GSK 3α enzyme isoform (Life Technologies) were evaluated in a similar fashion to that described hereinabove. The GSK3α protein (500 ng/mL, 2.5 µL) was incubated with the test compound (2.5 µL at either 40 µg/mL, 12 µg/mL, 4 µg/mL, 1.2 µg/mL, 0.4 µg/mL, 0.12 µg/mL, 0.04 µg/mL, 0.012 µg/mL, 0.004 µg/mL or 0.0012 µg/mL) for 2 h at RT. The FRET peptide (8 µM, 2.5 µL), which is a phosphorylation target for GSK3a, and ATP (40 µM, 2.5 µL) were then added to the enzyme/compound mixture and the resulting mixture incubated for 1 h at RT. Development reagent (protease, 5 µL) was added for 1 h prior to detection in a fluorescence microplate reader (EnVision, Perkin Elmer).

In all cases, the site-specific protease cleaves non-phosphorylated peptide only and eliminates the FRET signal. Phosphorylation levels of each reaction were calculated using the ratio of coumarin emission (donor) over fluorescein emission (acceptor), for which low ratios indicate high phosphorylation and high ratios indicate low phosphorylation levels. The percentage inhibition of each reaction was calculated relative to non-inhibited control and the 50% inhibitory concentration ($IC_{50}$ value) was then calculated from the concentration-response curve.

Cellular Assays (Employed in the Examples)

The following cellular assays were employed to assess the compound of the present invention and the results are given infra.

LPS-induced TNFα/IL-8 Release in d-U937Cells

U937 cells, a human monocytic cell line, were differentiated into macrophage-type cells by incubation with PMA (100 - 200 ng/mL) for 48 to 72 hr. Cells were pre-incubated with final concentrations of test compound for 2 h and were then stimulated with LPS (0.1 µg/mL; from *E. Coli:* O111: B4, Sigma) for 4 h. The supernatant was collected for determination of TNFα and IL-8 concentrations by sandwich ELISA (Duo-set, R&D systems). The inhibition of TNFα production was calculated as a percentage of that achieved by 10 µg/mL of BIRB796 at each concentration of test compound by comparison against vehicle control. The relative 50% effective concentration ($REC_{50}$) was determined from the resultant concentration-response curve. The inhibition of IL-8 production was calculated at each concentration of test compound by comparison with vehicle control. The 50% inhibitory concentration ($IC_{50}$) was determined from the resultant concentration-response curve.

Poly I:C-induced ICAM-1 Expression in BEAS2B Cells

Poly I:C was used in these studies as a simple, RNA virus mimic. Poly I:C-Oligofectamine mixture (2% Oligofectamine ±1 µg/mL Poly I:C, 25 µL; Life Technologies and Invivogen Ltd., San Diego, Calif., respectively) was transfected into BEAS2B cells (human bronchial epithelial cells, ATCC). Cells were pre-incubated with final concentrations of test compounds for 2 h and the level of ICAM-1 expression on the cell surface was determined by cell-based ELISA. At a time point 18 h after poly I:C transfection, cells were fixed with 4% formaldehyde in PBS (100 μL) and then endogenous peroxidase was quenched by the addition of washing buffer (100 μL, 0.05% Tween in PBS: PBS-Tween) containing 0.1% sodium azide and 1% hydrogen peroxide. Cells were washed with wash-buffer (3×200 μL). After blocking the wells with 5% milk in PBS-Tween (100 μL) for 1 h, the cells were incubated with anti-human ICAM-1 antibody (50 μL; Cell Signaling Technology, Danvers, Mass.) in 1% BSA PBS overnight at 4° C.

The cells were washed with PBS-Tween (3×200 μL) and incubated with the secondary antibody (100 μL; HRP-conjugated anti-rabbit IgG, Dako Ltd., Glostrup, Denmark). The cells were then incubated with of substrate (50 μL) for 2-20 min, followed by the addition of stop solution (50 μL, 1N $H_2SO_4$).The ICAM-1 signal was detected by reading the absorbance at 450 nm against a reference wavelength of 655 nm using a spectrophotometer. The cells were then washed with PBS-Tween (3×200 μL) and total cell numbers in each well were determined by reading absorbance at 595 nm after Crystal Violet staining (50 μL of a 2% solution in PBS) and elution by 1% SDS solution (100 μL) in PBS. The measured OD 450-655 readings were corrected for cell number by dividing with the OD595 reading in each well. The inhibition of ICAM-1 expression was calculated at each concentration of test compound by comparison with vehicle control. The 50% inhibitory concentration ($IC_{50}$) was determined from the resultant concentration-response curve.

Cell Mitosis Assay

Peripheral blood mononucleocytes (PBMCs) from healthy subjects were separated from whole blood (Quintiles, London, UK) using a density gradient (Histopaque®-1077, Sigma-Aldrich, Poole, UK). The PBMCs (3 million cells per sample) were subsequently treated with 2% PHA (Sigma-Aldrich, Poole, UK) for 48 h, followed by a 20 h exposure to varying concentrations of test compounds. At 2 h before collection, PBMCs were treated with demecolcine (0.1 μg/mL; Life Technologies, Paisley, UK,) to arrest cells in metaphase. To observe mitotic cells, PBMCs were permeabilised and fixed by adding Intraprep (50 μL; Beckman Coulter, France), and stained with anti-phospho-histone 3 (0.26 ng/L; #9701; Cell Signalling) and propidium iodide (1 mg/mL; Sigma-Aldrich as previously described (Muehlbauer P. A. et al., Mutation Res., 2003, 537, 117-130). Fluorescence was observed using an ATTUNE flow cytometer (Life Technologies), gating for lymphocytes. The percentage inhibition of mitosis was calculated for each treatment relative to vehicle (0.5% DMSO) treatment.

The Effect of Test Compounds on Cell Viability: MTT Assay

Differentiated U937 cells were pre-incubated with each test compound (final concentration 10 pg/mL in 200 μL media indicated below) under two protocols: the first for 4 h in 5% FCS RPMI1640 media and the second in 10% FCS RPMI1640 media for 24 h. The supernatant was replaced with new media (200 μL) and MTT stock solution (10 μL, 5 mg/mL) was added to each well. After incubation for 1 h the media were removed, DMSO (200 μL) was added to each well and the plates were shaken lightly for 1 h prior to reading the absorbance at 550 nm. The percentage loss of cell viability was calculated for each well relative to vehicle (0.5% DMSO) treatment. Consequently an apparent increase in cell viability for drug treatment relative to vehicle is tabulated as a negative percentage.

Cytokine Production in LPS-Treated Sputum Macrophages from COPD Patients

Patients with COPD inhaled a nebulised solution of 3% (w/v) hypertonic saline using an ultrasonic nebuliser (Devilbiss, Carthage, Mo.) with tidal breathing for 5 min. This procedure was repeated a maximum of three times until enough sputum was obtained. The sputum samples were homogenized and mixed vigorously using a vortex mixer in 0.02% v/v dithiothreitol (DTT) solution. The samples were re-suspended in PBS (40 mL) followed by centrifugation at 1500 rpm at 4° C. for 10 min to obtain sputum cell pellets. The pellets were washed with PBS (40mL). The sputum cells were then re-suspended in 4 mL macrophage serum-free medium (macrophage-SFM, Life technologies, containing 20 U/mL penicillin, 0.02 mg/mL streptomycin and 5 μg/mL amphotericin B) and seeded on high bound 96-well plate, followed by incubation for 1 h at 37° C. and at 5% $CO_2$ to allow the macrophages to attach to the bottom of the plate. The cells on the plate were washed with fresh macrophage-SFM (200 pUwell) to remove neutrophils and other contaminated cells. The adherent cells (mainly sputum macrophages) on the plate were used for further analysis. Sputum inductions were conducted in Quintiles Drug Research Unit at Guys Hospital and ethics approval and written informed consent was obtained by Quintiles.

Where appropriate, 1 μL of a solution containing either the test compound or reference article at the stated concentrations (either 0.1 μg/mL, 0.01 μg/mL, or 0.001 μg/mL) or alternatively 1 μL of DMSO as the vehicle control was added to each well (200 μL in media) and the cells were incubated for 2 h. The cells were stimulated with LPS solution (50 μL, final concentration: 1 μg/mL) and incubated for 18 h at 37° C. and 5% $CO_2$. The supernatant was then collected and kept at −80° C. Suitable luminex kits were used to measure the selected analytes. After thawing the supernatant, the magnetic antibody beads were multiplexed and incubated in a 96-well plate with standard, background solution or the appropriate volume of sample overnight with shaking at 4° C. After washing twice with 200 μL of wash buffer provided by the kit per well using a magnetic plate washer, the beads were incubated for 1 h at RT with the biotin conjugated antibody solution provided by the kit with shaking. Streptavidin solution was added for 30 min with shaking at RT. After washing with 200 μL wash buffer per well, the beads were resuspended in sheath fluid (150 μL) and analyzed immediately. The level of each analyte in the supernatant was calculated using Xcel Fit software with a 4 or 5-parameter equation using each standard curve. The inhibitions of each cytokine production were calculated at each concentration by comparison with vehicle control.

Rhinovirus-Induced IL-8 Release

Human rhinovirus RV16 is obtained from the American Type Culture Collection (Manassas, Va.). Viral stocks are generated by infecting MRC5 cells with HRV until 80% of the cells were cytopathic.

BEAS2B cells are infected with HRV at an MOI of 1.2 and incubated for 1 h at 33° C. with gentle shaking for to promote absorption. The cells are then washed with PBS, fresh media added and the cells are incubated for a further 72 h. The supernatant is collected for assay of IL-8 concentrations using a Duoset ELISA development kit (R&D systems, Minneapolis, Minn.). Compounds are added 2 h before HRV infection and 1 h after infection when non-infected HRV is washed out.

Cellular Assays (Not Employed in the Examples)

The following cellular assays could be employed to assess the compound of the present invention:

Rhinovirus-induced IL-8 Release (variation on the above method) and ICAM-1 Expression Human rhinovirus RV16 is obtained from the American Type Culture Collection (Manassas, Va.). Viral stocks are generated by infecting Hela cells with HRV until 80% of the cells were cytopathic.

BEAS2B cells are infected with HRV at an MOI of 5 and incubated for 1 to 2 h at 33° C. with gentle shaking to promote absorption. The cells are then washed with PBS, fresh media added and the cells are incubated for a further 72 h. The supernatant is collected for assay of IL-8 concentrations using a Duoset ELISA development kit (R&D systems, Minneapolis, Minn.).

The level of cell surface ICAM-1 expression is determined by cell-based ELISA. At 72 h after infection, cells were fixed with 4% formaldehyde in PBS. After quenching endogenous peroxidase by adding 0.1% sodium azide and 1% hydrogen peroxide, wells are washed with wash-buffer (0.05% Tween in PBS: PBS-Tween). After blocking well with 5% milk in PBS-Tween for 1 h, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well were determined by reading absorbance at 595 nm after Crystal Violet staining and elution by 1% SDS solution. The measured $OD_{450\text{-}655}$ readings are corrected for cell number by dividing with the $OD_{595}$ reading in each well. Compounds are added 2 h before HRV infection and 1 to 2 h after infection when non-infected HRV is washed out.

LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 h before addition of 1 ng/mL LPS (*Escherichia Coli* 0111:B4 from Sigma Aldrich) for 24 h under normal tissue culture conditions (37° C., 5%$CO_2$). The supernatant is harvested for determination of and TNFα concentrations by sandwich ELISA (Duo-set, R&D systems) and read on the fluorescence microplate reader (Varioskan® Flash, ThermoFisher Scientific).

The concentration at 50% inhibition ($IC_{50}$) of IL-8 and TNFa production is calculated from the dose response curve.

IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD28 monoclonal antibodies (0.3 μg/mL eBioscience and 3 μg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

IL-1β-induced IL-8 Release in HT29 Cells

HT29 cells, a human colon adenocarcinoma cell line, are plated in a 96 well plate (24 h) and pre-treated with compounds at the desired concentration for 2 h before addition of 5 ng/mL of IL-1β (Abcam) for 24 h, Supernatants are harvested for IL-8 quantification by Sandwich ELISA (Duo-set, R&D System). The $IC_{50}$ is determined from the dose response curve.

T Cell Proliferation

PBMCs from Healthy Subjects are Separated from Whole Blood using a Density Gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at 2×10⁵ cells per well in 100 μL RPMI/10%FBS on 96 well flat bottomed plate (Corning Costar). 25 μL of test compound are diluted to the appropriate concentration (8× final conc.) in normal medium and added to duplicate wells on the plate to achieve a dose response range of 0.03 ng/mL-250 ng/mL. DMSO is added as a negative control. Plates are allowed to pre-incubate for 2 h before stimulation with 1 μg/mL anti-CD3 (OKT3; eBioscience). After 72 h, the medium in each well is replaced with 150 μL of fresh medium containing 10 μM BrdU (Roche). After 16 h, the supernatant is removed, the plate is dried and the cells fixed by adding 100 μL of fix/denature solution to each well for 20 min as per the manufacturer's instructions (Roche). Plates are washed once with PBS before addition of the anti-BrdU detection antibody and incubated for 90 min at room temperature. Plates are then washed gently 3× with the wash buffer supplied and developed by addition of 100 μL of substrate solution. The reaction is stopped by addition of 50 μL of 1 M $H_2SO_4$, and read for absorbance at 450 nm on a plate reader (Varioskan® Flash, ThermoFisher Scientific). The $IC_{50}$ is determined from the dose response curve.

Human Biopsy Assay

Intestinal mucosa biopsies are obtained from the inflamed regions of the colon of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 h in the organ culture chamber. The supernatant is harvested for determination of IL-6, IL-8, IL-1β and TNFα levels by R&D ELISA. Percentage inhibition of cytokine release by the test compounds is calculated relative to the cytokine release determined for the DMSO control (100%).

IL-2 and IFNγ Release in CD3/CD28 Stimulated LPMC cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments 3-4 mm size. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 μm cell strainer, washed twice, resuspended in RPMI- 1640 medium (Sigma-Aldrich) containing 10% fetal calf serum, 100 U/mL penicillin and 100 µg/mL streptomycin, and used for cell culture.

Freshly isolated LPMCs ($2\times10^5$ cells/well) are stimulated with 1 µg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

Inhibition of Cytokine Release from Myofibroblasts Isolated from IBD Patients

Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 µg/mL streptomycin, 50 µg/mL gentamycin, and 1 µg/mL amphotericin (Sigma-Aldrich). Established colonies of myofibroblasts are seeded into 25-$cm^2$ culture flasks and cultured in DMEM supplemented with 20% FBS and antibiotics to at least passage 4 to provide a sufficient quantity for use in stimulation experiments.

Subconfluent monolayers of myofibroblasts are then seeded in 12-well plates at $3\times10^5$ cells per well are starved in serum-free medium for 24 h at 37° C., 5% $CO_2$ before being cultured for 24 h in the presence of either DMSO control or appropriate concentrations of compound. After 24 h the supernatant is removed and assayed for the presence of IL-8 and IL-6 by R&D ELISA. Percentage inhibition of cytokine release by the test compounds is calculated relative to the cytokine release determined for the DMSO control (100%).

Human Neutrophil Degranulation

Neutrophils are isolated from human peripheral blood as follows:

Blood is collected by venepuncture and anti-coagulated by addition of 1:1 EDTA: sterile phosphate buffered saline (PBS, no Ca+/Mg+). Dextran (3% w/v) is added (1 part dextran solution to 4 parts blood) and the blood allowed to stand for approximately 20 min at RT. The supernatant is carefully layered on a density gradient (Lymphoprep, Axis-Shield Healthcare) and centrifuged (15 min, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 min, 1200 rpm). Cells are re-suspended in HBSS+(Hank's balanced salt solution (without phenol red) containing cytochalasin B (5 µg/mL) and 1 mM $CaCl_2$) to achieve $5\times10^6$ cells/mL.

$5\times10^4$ cells are added to each well of a V-bottom 96 well plate and incubated (30 min, 37° C.) with the appropriate concentration of test compound (0.3-1000 ng/mL) or vehicle (DMSO, 0.5% final conc). Degranulation is stimulated by addition of fMLP (final conc 1 µM) which after a further incubation (30 min, 37° C.) the cells are removed by centrifugation (5 min, 1500 rpm) and the supernatants transferred to a flat bottom 96 well plate. An equal volume of tetramethylbenzidine (TMB) is added and after 10 min the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

Cell Cytotoxicity Assay $5\times10^4$ TK6 cells (lymphoblastic T cell line) are added to the appropriate number of wells of a 96 well plate in 195 µL of media (RPMI) supplemented with 10% foetal bovine serum). 5 µL of DMSO control (final concentration 0.5% v/v) or test compound (final concentration either 5 or 1 µg/mL) is added to the wells and incubated at 37° C., 5% $CO_2$. After 24 h, the plate is centrifuged at 1300 rpm for 3 min and the supernatant discarded. Cells are then resuspended in 7.5 µg/mL propidium iodide (PI) in PBS. After 15 min, cells are analysed by flow cytometry (BD accuri). The % viability is calculated as the % of cells that are PI negative in the test wells normalised to the DMSO control.

In Vivo Screening: Pharmacodynamics and Anti-inflammatory Activity (Employed in the Examples)

The following in vivo screens were employed to assess the compound of the present invention and the results are given infra.

LPS-Induced Neutrophil Accumulation in Mice

Non-fasted Balb/c mice were dosed by the intra tracheal route with either vehicle, or the test substance at the indicated times (within the range 2-8 h) before stimulation of the inflammatory response by application of an LPS challenge. At T=0, mice were placed into an exposure chamber and exposed to LPS (7.0 mL, 0.5 mg/mL solution in PBS for 30 min). After a further 8 h the animals were anesthetized, their tracheas cannulated and BALF extracted by infusing and then withdrawing from their lungs 1.0 mL of PBS via the tracheal catheter. Total and differential white cell counts in the BALF samples were measured using a Neubaur haemocytometer. Cytospin smears of the BALF samples were prepared by centrifugation at 200 rpm for 5 min at RT and stained using a DiffQuik stain system (Dade Behring). Cells were counted using oil immersion microscopy. Data for neutrophil numbers in BAL are shown as mean±S.E.M. (standard error of the mean). The percentage inhibition of neutrophil accumulation was calculated for each treatment relative to vehicle treatment.

Cigarette Smoke Model

A/J mice (males, 5 weeks old) were exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances were administered intra-nasally (35 µL of solution in 10% DMSO/PBS) once daily for 3 days after the final cigarette smoke exposure. At 12 h after the last dosing, each of the animals was anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil). BALF was centrifuged and the supernatant was collected. The level of keratinocyte chemoattractant (KC; CXCL1) in BALF was quantitated using a Quantikine® mouse KC ELISA kit (R&D systems, Inc., Minneapolis, Minn., USA).

In Vivo Screening: Pharmacodynamics and Anti-inflammatory Activity (not employed in the Examples)

The following in vivo screens could be employed to assess the compound of the present invention:

DSS-Induced Colitis in Mice

Non-fasted, 10-12 week old, male BDF1 mice are dosed by oral gavage twice daily with either vehicle, reference item (5-ASA) or test compound one day before (Day -1) stimulation of the inflammatory response by treatment with DSS. On Day 0 of the study DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study animals are weighed every day and stool observations are made and recorded as a score, based on stool consistency. At the time of sacrifice on Day +6 the large intestine is removed and the length and weight are recorded. Sections of the colon are taken for either MPO analysis to determine neutrophil infiltration or for histopathology scoring to determine disease severity.

TNBS-Induced Ccolitis in Mice

Non-fasted, 10-12 week old, male BDF1 mice are dosed by oral gavage twice daily with either vehicle (5 mL/kg), reference item (Budesonide 2.5 mg/kg) or test compound (1, 5 or 50 mg/kg) one day before (Day -1) stimulation of the inflammatory response by treatment with 2,4,6-trinitrobenzenesulphonic acid (TNBS) (15 mg/mL in 50% ethanol/50% saline). On Day 0 of the study TNBS (200 µL) is administered intra-colonically via a plastic catheter followed by BID dosing of the vehicle, reference or test compound for 2 or 4 days. During the study animals are weighed every day and stool observations are made and recorded as a score, based on stool consistency. At the time of sacrifice on Day 2 (or Day 4) the large intestine is removed and the length and weight recorded. Sections of the colon are taken for either MPO analysis to determine neutrophil infiltration or for histopathology involving scoring to determine disease severity.

Adoptive Transfer in Mice

On study day 0, female Balb/C mice are terminated and spleens obtained for $CD45R^{high}$ cell isolation (Using SCID IBD cell Separation protocol). Approximately $4 \times 10^5$ cells/mL $CD45RB^{high}$ cells are then injected IP (100 µL/mouse) into female SCID animals. On study day 14, mice are weighed and randomized into treatment groups based on body weight. On day 21, compounds are administered BID, via oral gavage, in a peanut oil vehicle at the dose levels outlined below and a dose volume of 5 mL/kg. Treatment continues until study day 42, at which point the animals are necropsied 4 h after a.m. administration. The colon length and weight is recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between naïve animals and vehicle animals, where higher inhibition implies closer to the non-diseased, naïve, phenotype.

In Vitro and In Vivo Screening Results

In vitro screening results for the compound of the invention (free base form) are set out in Table 2, Table 3, Table 4 and Table 5 below and FIG. 9. Comparison is made with a structurally related Reference Compound N-(4-(4-(3-(3-tert-Butyl-1-p-tolyl-1H-pyrazol-5-yl)ureido)naphthalen-1-yloxy)pyridin-2-yl)-2-methoxyacetamide (Example 1 of WO2010/112936), which has been previously described as a potent anti-inflammatory agent with anti-viral effects, as well as with fluticasone propionate which is a well known anti-inflammatory agent.

TABLE 2 p38 MAPKα and γ, HCK, c-Src, Syk and GSK3α Enzyme Profile of Test Compounds

| | $IC_{50}$ Values for Enzyme Inhibition (nM) | | | | | |
|---|---|---|---|---|---|---|
| Test Compound | p38 MAPKα | p38 MAPKγ | HCK | c-Src | Syk | GSK3α |
| Reference Compound | 10 | 87 | 7 | 11 | 42 | 18 |
| Compound of the invention | 26 | 152 | 55 | 199 | >15955 | >15105 |

TABLE 3

Inhibition of LPS Induced TNFα and IL-8 Release and PolyIC Induced ICAM-Expression for Test Compounds

| | LPS Induced Release (nM) | | |
|---|---|---|---|
| Test Compound | IL-8 $IC_{50}$ (dU937) | TNFα $REC_{50}$ (dU937) | PolyIC/ ICAM1 (nM) $IC_{50}$ (BEAS2B) |
| Reference Compound | 1.2 | 0.7 | 3.8 |
| Compound of the invention | 11.4 | 5.5 | 61.1 |

TABLE 4

Effect of Test Compounds on Cell Viability

| | MTT Assay[1] Cell viability at time point indicated in d-U937 Cells | | Mitosis Assay[2] Inhibition (%) of mitosis |
|---|---|---|---|
| Test Compound | 4 h | 24 h | At 5 ug/mL |
| Reference Compound | − | + | 93 ± 5 |
| Compound of the invention | − | − | 18 ± 7 |

[1]Cell viability screen: −ve and +ve indicate the value is below and above, respectively, the no significant effect threshold defined as 30% inhibition at 10 µg/mL at the time point indicated.
[2]Mean ± SEM

TABLE 5

Effect of Test Compounds on cytokine production in LPS-treated sputum macrophages from COPD patients

| Test Compound | Percent Inhibition at 0.1 µg/mL IL-6 |
|---|---|
| Fluticasone propionate | 29 ± 21 |
| Compound of the invention | 48 ± 9 |

Summary of In Vitro and In Vivo Screening Results

The compound of the invention demonstrates a profile in in vitro and in vivo assays consistent with good anti-inflammatory activity. It has very weak activity at Syk and GSK3a kinases (Tables 2 and 3).

The compound of the invention shows markedly less activity in assay systems that measure its impact on cell viability indicating that it is likely to possess a superior therapeutic index over the Reference Compound (Table 4).

The compound of the invention showed superior anti-inflammatory activity compared to fluticasone propionate in the assay system used (Table 5).

Figure 9:
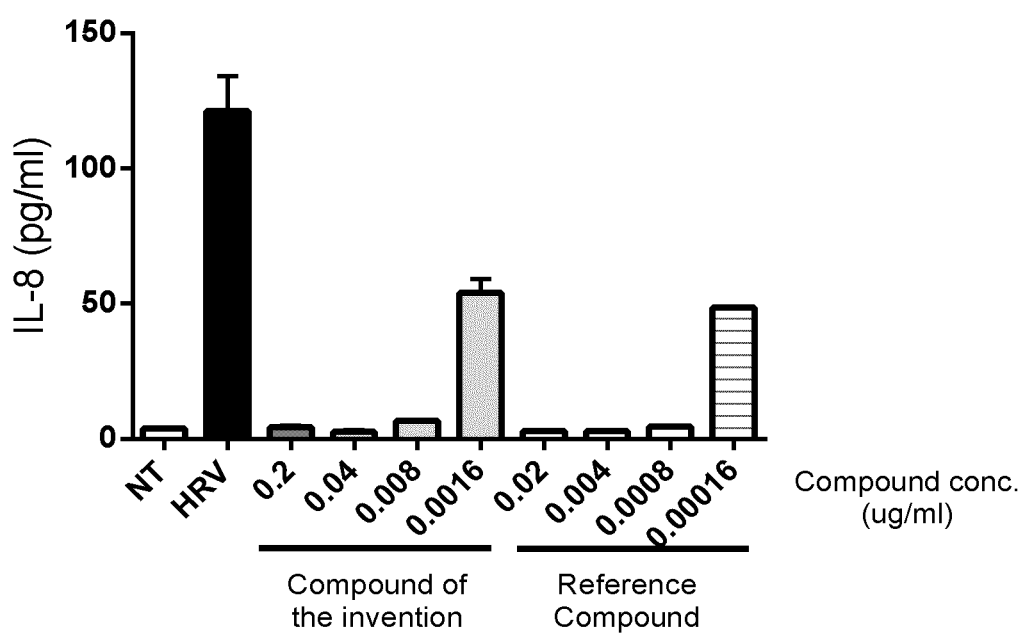
FIG. 9 shows the effect of test compounds on rhinovirus-induced IL-8 Release in BEAS2B cells

The compound of the invention shows dose-dependent inhibition of HRV-induced IL-8 (FIG. 9).

In summary, these results suggest that the compound of the invention has similar anti-inflammatory properties to the Reference Compound disclosed above and, advantageously, is associated with a superior therapeutic index.

What is claimed is:

1. A compound of formula (XV):

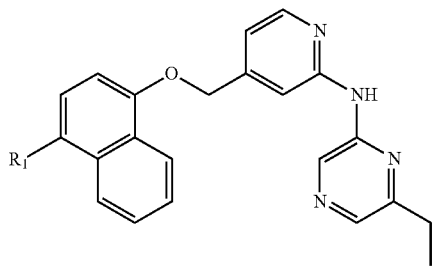

(XV)

wherein $R_1$ represents an amino group, a protected amino group or nitro group;
or a salt thereof.

2. A compound of formula (XV) according to claim 1 which is a compound of formula (VIII):

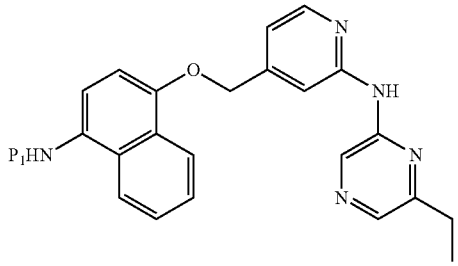

(VIII)

wherein $P_1$ represents an amine protecting group;
or a salt thereof.

3. A compound according to claim 2 wherein the amine protecting group is t-butyloxycarbonyl.

4. A compound of formula (XV) according to claim 1 which is a compound of formula (III):

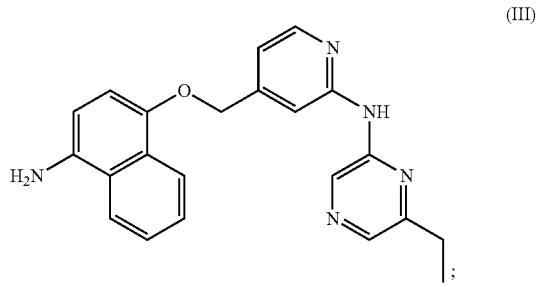 [SMILES: CCc1cncc(Nc2cc(COc3ccc(N)c4ccccc34)ccn2)n1]

(III)

or a salt thereof.

5. A compound of formula (XV) according to claim 1 which is a compound of formula (VII):

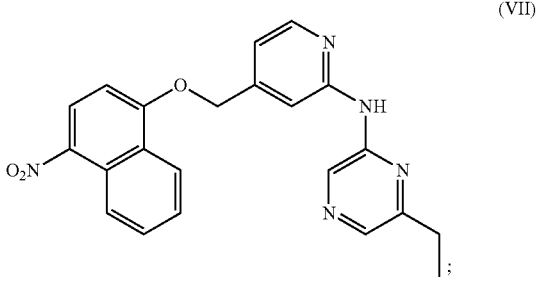 [SMILES: CCc1cncc(Nc2cc(COc3ccc([N+](=O)[O-])c4ccccc34)ccn2)n1]

(VII)

or a salt thereof.

* * * * *